United States Patent
Yokoyama et al.

(10) Patent No.: US 7,337,098 B2
(45) Date of Patent: Feb. 26, 2008

(54) DIFFRACTION CONDITION SIMULATION DEVICE, DIFFRACTION MEASUREMENT SYSTEM, AND CRYSTAL ANALYSIS SYSTEM

(75) Inventors: Ryouichi Yokoyama, Tokyo (JP); Kamihisa Endo, Tokyo (JP); Tetsuya Ozawa, Tokyo (JP); Jimpei Harada, Tokyo (JP)

(73) Assignee: Rigaku Corporation, Tokyo (JP)

( * ) Notice: Subject to any disclaimer, the term of this patent is extended or adjusted under 35 U.S.C. 154(b) by 792 days.

(21) Appl. No.: 10/109,688

(22) Filed: Apr. 1, 2002

(65) Prior Publication Data

US 2003/0009316 A1   Jan. 9, 2003

Related U.S. Application Data

(63) Continuation-in-part of application No. 09/312,053, filed on May 17, 1999, now abandoned.

(30) Foreign Application Priority Data

May 18, 1998 (JP) ................. 10-135297
May 12, 1999 (JP) ................. 11-131906

(51) Int. Cl.
  *G06G 7/48* (2006.01)
  *G01N 23/207* (2006.01)
(52) U.S. Cl. ............................ 703/6; 378/73
(58) Field of Classification Search .............. 703/6; 378/73
  See application file for complete search history.

(56) References Cited

U.S. PATENT DOCUMENTS

| | | | |
|---|---|---|---|
| 3,816,747 A | 6/1974 | Kishino | |
| 4,426,719 A | 1/1984 | Fraenkel | |
| 5,365,456 A | 11/1994 | Subbiah | |
| 5,371,778 A | 12/1994 | Yanof et al. | |
| 5,455,952 A | 10/1995 | Gjovaag | |
| 5,631,974 A | 5/1997 | Lau-Kee | |
| 5,916,163 A | 6/1999 | Panescu et al. | |
| 5,986,662 A | 11/1999 | Argiro et al. | |
| 6,006,126 A | 12/1999 | Cosman | |
| 6,008,808 A | 12/1999 | Almeida et al. | |
| 6,051,834 A | 4/2000 | Kakibayashi et al. | |
| 6,052,476 A | 4/2000 | Qian et al. | |
| 6,071,288 A | 6/2000 | Carol et al. | |

OTHER PUBLICATIONS

Izumi: Rietan: a software package for the rietveld analysis and simulation of x-ray and neutron diffraction patterns; pp. 10-20; The Rigaku Journal; 1989.*

Koppensteiner et al.; Investigation of strain-symmetrized and pseudomorphic SiGe superlattices by x-ray reciprocal space mapping; pp. 3489-3501; J. Appl. Phys.; 1994.*

(Continued)

*Primary Examiner*—Hugh Jones
(74) *Attorney, Agent, or Firm*—Wenderoth, Lind & Ponack, L.L.P.

(57) ABSTRACT

A diffraction condition simulation device capable of calculating the UB matrix and the rotation matrix R and also their multiplication RUB, thereby obtaining and displaying any Bragg reflection conditions of any Bragg reflections desired by an operator of said device. The Bragg reflection conditions are useful for structure analysis and structure evaluation of any crystal samples.

21 Claims, 16 Drawing Sheets

OTHER PUBLICATIONS

Busing et al.; Angle calculations for 3- and 4- circle x-ray and neutron diffractometers; pp. 457-464; Acta Cryst.; 1967.*
PC-MRD User Guide; pp. 1-1 to 6-20; Philips Electronics; 1993.*
Yokoyama et al.; Determination of the orientation of an epitaxial thin film by a new computer program CrystalGuide; pp. 46-52; Jan. 1999; The Rigaku Journal.*
ATX-G: Product Information; pp. 53-58; Rigaku journal; Jan. 1999.*
Omar; Elementray Solid State Physics; Chapter 2; Adidson-Wesley; 1975.*
Calculation of Structure factors; pp. 1-4; www.ruppweb.org/Xray/comp/strufac; Mar. 1999.*
X-ray crystallograhpy; pp. 1-4; from Wikipedia; 2006.*
Introduction to the calculation of structure factors; pp. 1-11; 1997; obtained from www.iucr.org/iucr-top/comm/cteach/pamphlets/3/3.*
Jones et al.; Monte Carlo Investigation of electron-impact ionization in liquid Xenon; Phy. Rev. B; pp. 9382-9387; 1993.*
Phillips; XRayView: A Teaching Aid for X-Ray Crystallography; Biophysical Journal vol. 69 Oct. 1995 1281-1283.*
Johnson et al.; "A computational steering model applied to problems in medicine"; IEEE Proc. Supercomputing; pp. 540-549, 1994.
Parker et al.; "An integrated problem solving environment: the SCIRun computational steering system"; IEEE Systems Science; pp. 147-156, 1998.
Tsalpatouros et al.; "CT-based software for 3-D localization and reconstruction in stepping source brachytherapy"; IEEE Trans. Infor. Tech.; pp. 229-242, 1997.
Peterse et al.; "New application of classical x-ray diffraction methods for epitaxial firm characterization"; Thin Film Solids; pp. 49-53, 1996.
Sheehan et al.; "AVS software for visualization in molecular microscopy"; J. Structural Biology; pp. 99-106, 1996.
PC-MRD User Guide, Software for the Materials Research Diffractometer, First Edition, Mar. 1993.
Busing et al.; "Angle Calculations for 3- and 4- Circle X-ray and Neutron Diffractometers"; pp. 457-464, 1967.

* cited by examiner

DIFFRACTION CONDITION SIMULATION DEVICE, DIFFRACTION MEASUREMENT SYSTEM, AND CRYSTAL ANALYSIS SYSTEM

This application is a continuation-in-part of Ser. No. 09/312,053 filed May 17, 1999 now abandoned.

BACKGROUND OF THE INVENTION

1. Field of the Invention

The present invention relates to a diffraction condition simulation device, a diffraction measurement system, and a crystal analysis system. More particularly, the present invention relates to a novel diffraction condition simulation device, a diffraction measurement system, and a crystal analysis system which are useful for structure analysis and structure evaluation of a crystal sample such as a wafer for a semiconductor or a thin film deposited on the wafer.

2. Description of the Related Art

In crystal structure analysis developed as an analysis of atomic structure, X rays, or particle beams such as neutron beams or electron beams are applied to a crystal sample with an unknown structure, and then, using the diffraction phenomenon of rays scattered by the crystal-sample, the lattice type of the crystal sample or the atomic arrangement in the lattice are clarified. In this crystal structure analysis, for example, X rays are used for the analysis of the electron density of the crystal sample, neutron beams are used for the analysis of the atomic nuclei position of the crystal sample, and electron beams are used for the analysis of the electric potential of the crystal sample.

For such crystal structure analysis, diffraction condition simulation described below is frequently carried out. First, a reciprocal lattice intrinsic to a crystal is calculated on the basis of crystal information such as known lattice constants. Then, using this reciprocal lattice simulation, incident angles and outgoing angles of X ray or particle beams, or $\omega$ angles, $\chi$ angles, and $\phi$ angles as orientation angles of the crystal which satisfy Bragg scattering conditions, or intensity information are obtained.

However, in conventional simulation devices for carrying out such diffraction condition simulation, although a section of the limiting sphere containing reciprocal lattice points which express the Bragg reflection caused by a crystal sample is shown, the displayed section of the limiting sphere cannot be rotated freely and continuously in accordance with a crystal orientation. Thus, it has been impossible to display a desired reciprocal lattice quickly and easily.

Further, in general, there are innumerable diffraction conditions which cause one Bragg reflection, by rotating along a reciprocal lattice vector of a crystal, and the orientation angles, i.e., $\omega$ angle, $\chi$ angle, $\phi$ angle, of the crystal are determined for each of the innumerable diffraction conditions. However, the conventional device is limited to a reflection condition where the x angle of the crystal sample at a minimum, or to the symmetric reflection condition where the incident angle is the same as the outgoing angle, so that the orientation angles of the crystal obtained for one Bragg diffraction condition have been extremely limited.

Moreover, diffraction information obtained from simulation display of a conventional simulation device has been insufficient for the crystal structure analysis. For example, the intensity of the Bragg reflection cannot be obtained, nor can the Bragg reflection be displayed with any distinction between a reflection with the intensity of more than 0 (here, called a general reflection) and a forbidden reflection with the intensity which is theoretically 0, making it difficult to distinguish between the general reflection and the forbidden reflection.

Since the conventional simulation device has a lot of restrictions as to the display of reciprocal lattices or diffraction information as described above, it is earnestly desired to realize a device capable of carrying out improved diffraction condition simulation.

SUMMARY OF THE INVENTION

Here, the limiting sphere is, as exemplified in FIG. 1, a sphere which contains the reciprocal lattice points of the reciprocal lattice of a crystal sample, and has a radius of $2/\lambda \text{Å}^{-1}$ ($\lambda$, is a wavelength of X rays or particle beams) with a center at the origin o of the reciprocal lattice of the crystal sample. This limiting sphere indicates a range where an Ewald sphere (or called a reflection sphere) can be rotated, the Ewald sphere having a radius of $1/\lambda$ with a center A, of a generation source which emits X-ray or particle beams incident toward the origin o of the reciprocal lattice of the crystal sample and containing the origin o of the reciprocal lattice on its circumference. When the incident angle $\omega$ of the X rays or particle beams to a crystal sample (concretely, the origin o of the reciprocal lattice of the crystal sample ) is changed, the Ewald sphere rotates around the origin o of the reciprocal lattice in accordance with the incident angle $\omega$ within the limiting sphere, and when the Ewald sphere comes in contact with a reciprocal lattice point in the limiting sphere, that is, when the reciprocal lattice point is placed on the circumference of the Ewald sphere, the Bragg reflection of X rays or particle beams occurs from the position A toward the reciprocal lattice point placed on the circumference of the Ewald sphere. Incidentally, each of the reciprocal lattice points is normally labeled by Miller indices hkl as integers.

In an example shown in FIG. 1, the incidence of X rays or particle beams is indicated by a vector $k_0$, Bragg diffraction (that is, an outgoing reflection from the crystal) of the incident X rays or particle beams is expressed by a vector k, and a scattering vector equal to a difference between the vector $k_0$ and the vector k is expressed by Q. The Bragg reflection is labeled by a Miller indices of 004 (=hkl).

Incidentally, the foregoing $\chi$ angle and the $\phi$ angle of the crystal sample are, as exemplified in FIG. 1, a rotation angle of the crystal sample in the case where it rotates along an axis (X-axis in the drawing) parallel to the plane of the crystal sample, and a rotation angle of the crystal sample in the case where it rotates along an axis ($\Phi$-axis in the drawing) extending vertically to the plane of the crystal sample, respectively, and they are angles to determine the orientation of the crystal sample together with the $\omega$ angle used to determine the incident angle of X rays or particle beams to the crystal sample.

This invention has been made in view of the foregoing circumstances, and an object thereof is to provide a novel diffraction condition simulation device, a diffraction measurement system, and a crystal analysis system which overcome the problems of the prior art and are capable of quickly and easily calculating and displaying a desired Bragg reflection satisfying various diffraction conditions necessary for structure analysis and characterization of a crystal structure.

BRIEF DESCRIPTION OF THE DRAWINGS

The forgoing and other objects, features and advantages of the present invention will be apparent from the following more particular description of preferred embodiments of the invention, taken in conjunction with the accompanying drawings, in which.

DETAILED DESCRIPTION OF THE INVENTION

First Embodiment

Figure 2:
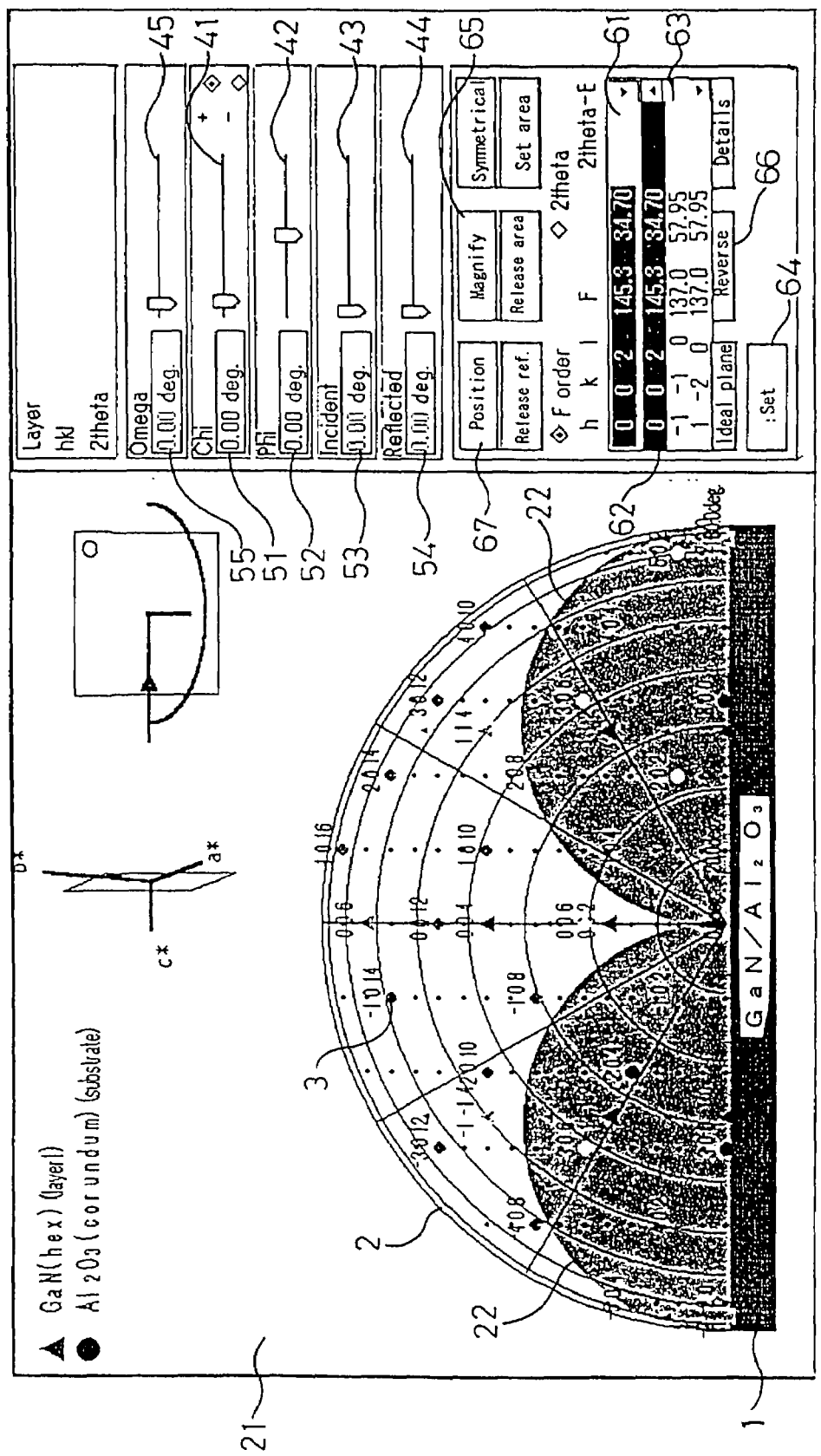
FIG. 2 is a view showing an example of a screen display of a computer by a diffraction condition simulation device of the present invention.
Figure 3:
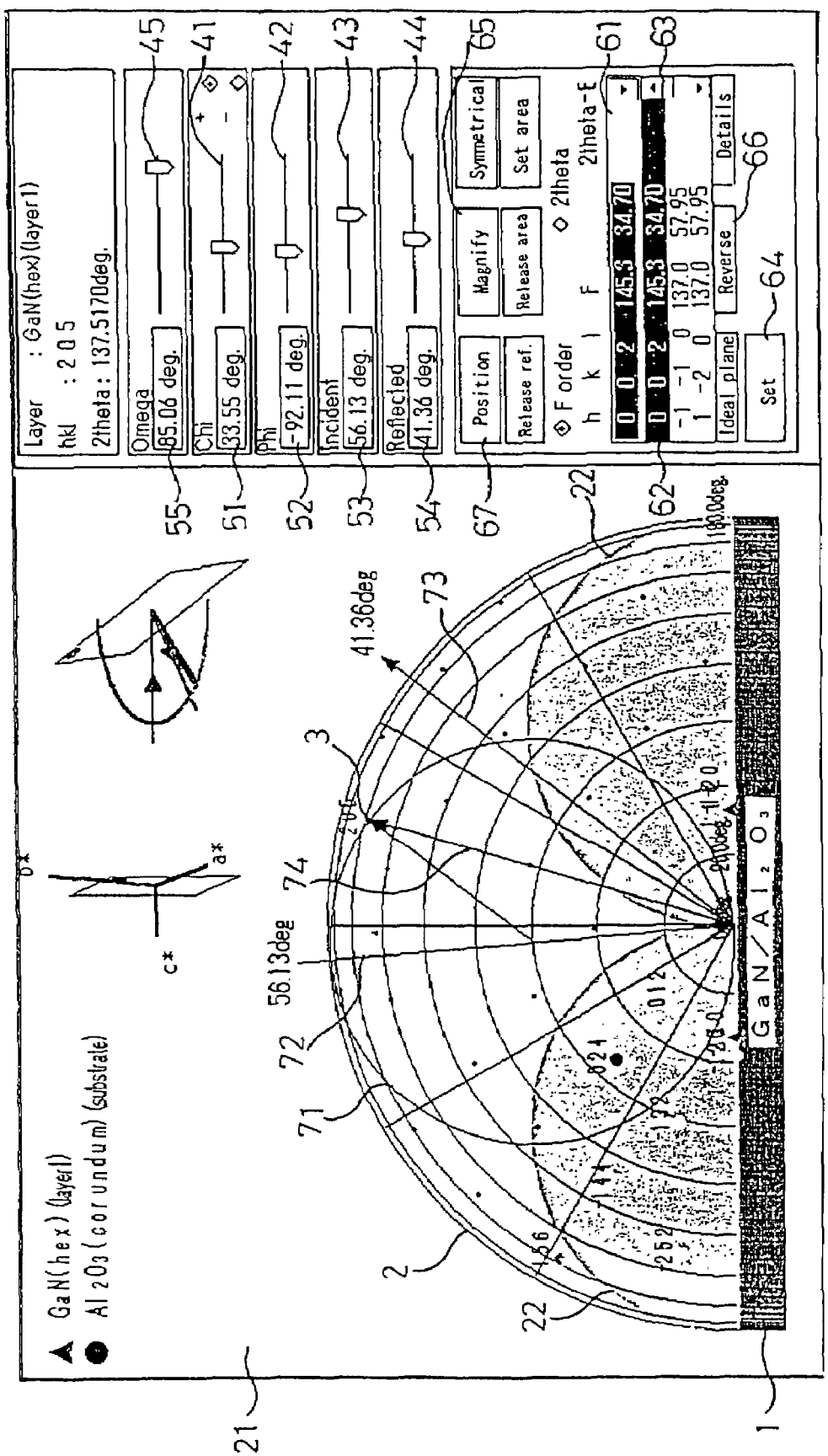
FIG. 3 is a view showing an example of a display of a Bragg reflection on the screen display of FIG. 2.
Figure 4:
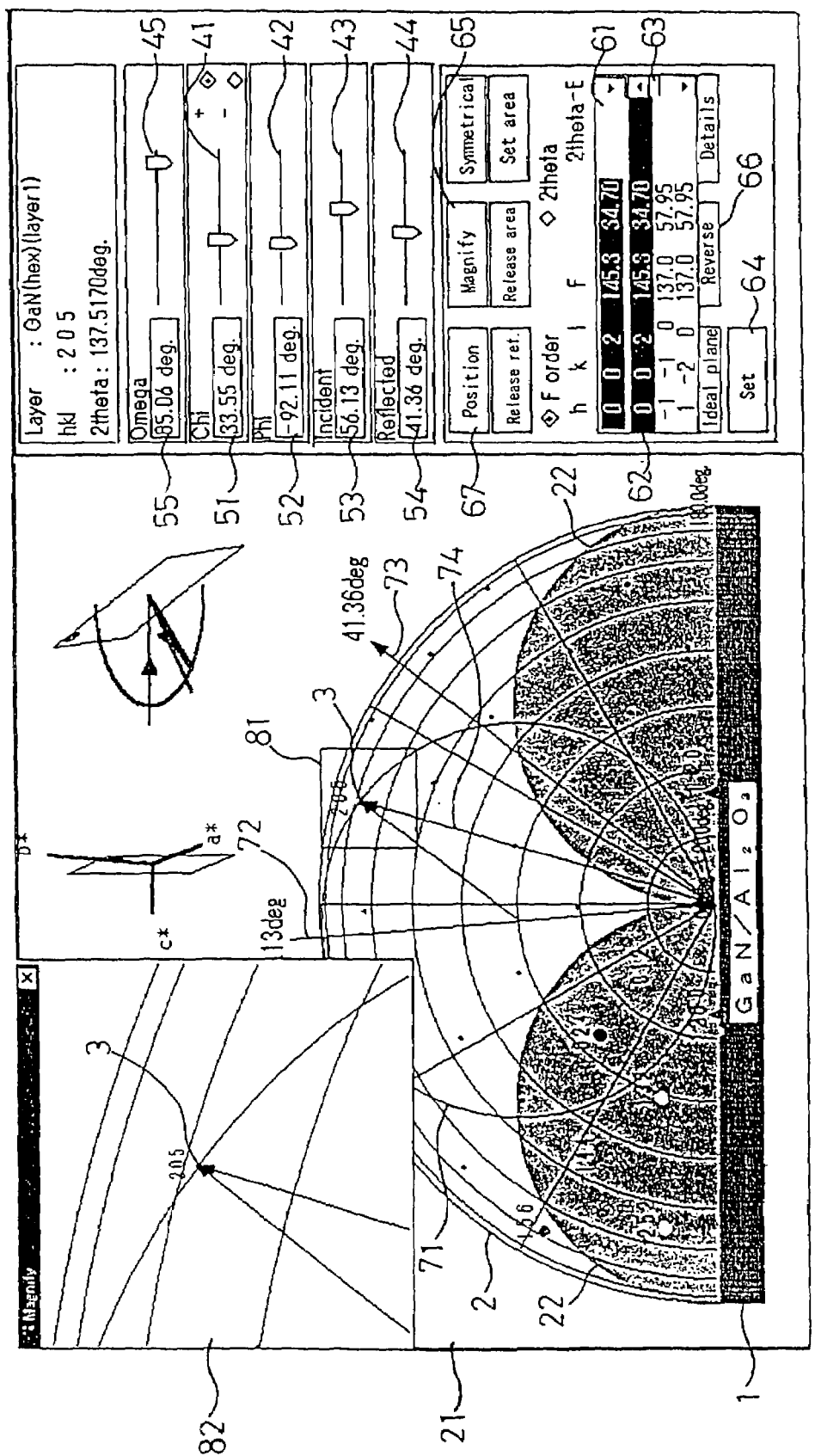
FIG. 4 is a view showing an example of an enlarged display of the Bragg reflection on the screen display of FIG. 2.
Figure 5:
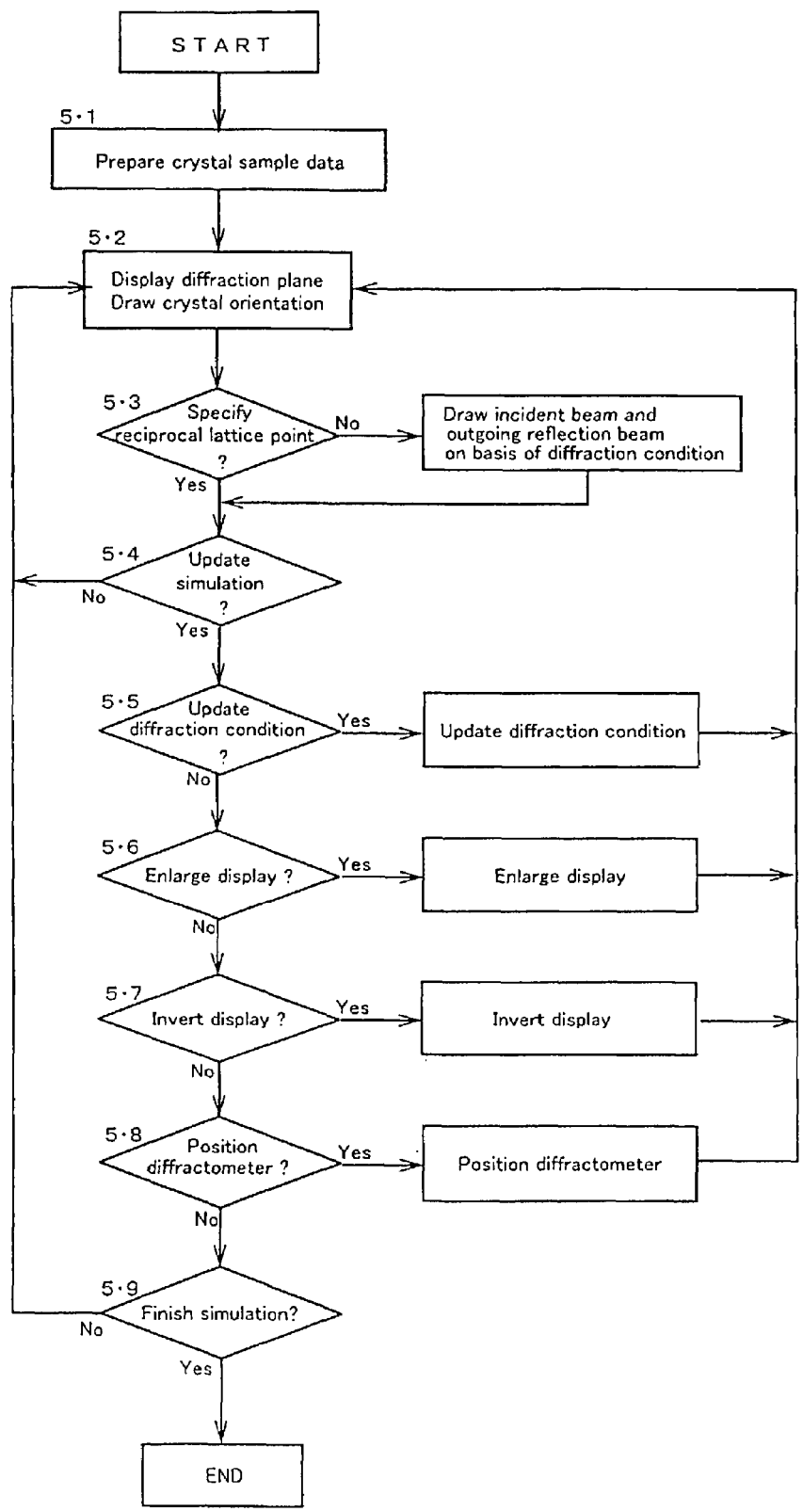
FIG. 5 shows an overall flow of simulation operation by a diffraction condition simulation device of the present invention.

FIGS. 2 to 4 show an embodiment of a computer screen display of a diffraction condition simulation device of this invention. In this embodiment, GaN/Al$_2$O$_3$ is used as a crystal sample, and X rays are used as an incident wave. FIG. 5 exemplifies the overall flow of simulation operation by the diffraction condition simulation device of this invention, and FIGS. 6 to 12 exemplify the detailed flow of each simulation operation in FIG. 5.

In the following, the diffraction condition simulation device of this invention will be described in detail along the rough flow of the simulation operation shown in FIG. 5 and using the detailed flow diagrams of FIGS. 6 to 12, while suitably referring to the examples of the computer screen displays of FIGS. 2 to 4.

Figure 6:
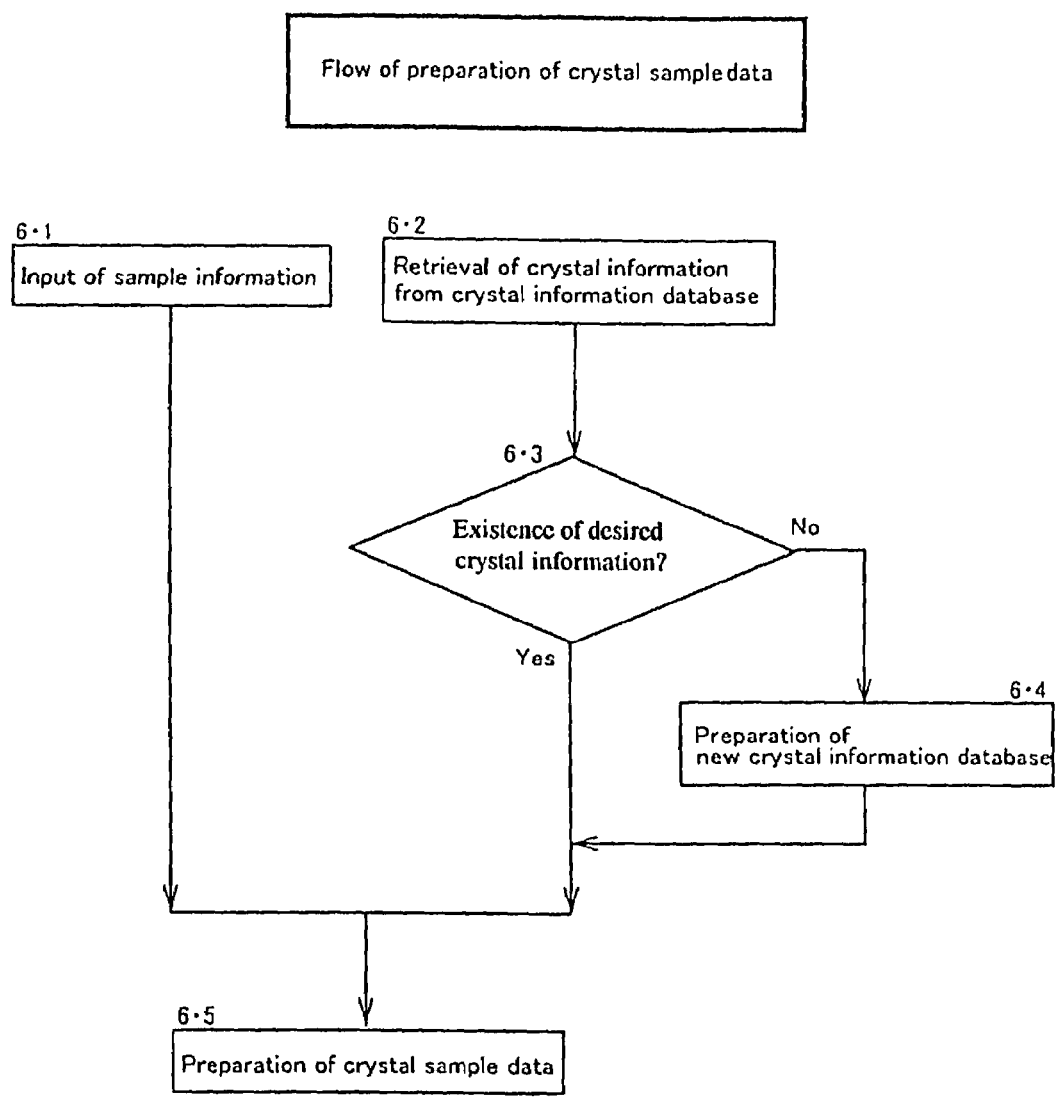
FIG. 6 shows an operational flow of crystal sample information input.

Flow of Preparation of Crystal Sample Data [FIG. 5, step 5•1; FIG. 6]

First, crystal sample data intrinsic to a crystal sample are prepared [step 5•1]. The crystal data are calculated, for example, as illustrated in the flow diagram exemplified in FIG. 6 by using information (hereinafter referred to as crystal information) intrinsic to the crystal constituting the crystal sample, such as a composition ratio in a case of a solid solution, space group, lattice constants, atomic positions in a crystal lattice, temperature factors, and elastic constants, and information (hereinafter referred to as sample information) non-intrinsic to the sample, such as a sample name, an orientation of the sample normal, and the incident direction of X rays or particle beams to the crystal sample. The calculated crystal sample data include the coordinates and the structure factors to all the reciprocal lattice points of the crystal sample, and the like.

More specifically, as exemplified in FIG. 6, the sample information of the crystal sample to be simulated is first inputted [step 6•1].

Furthermore, from an existing crystal information database (this crystal information database is, for example, previously stored in storage means) in which crystal information about various crystals constitutes a database, the crystal information about the crystal constituting the crystal sample is retrieved [step 6•1].

In this retrieval, if the desired crystal information does not exist in the existing crystal information data base [step 6•3 No], a crystal information database of the necessary crystal is newly prepared [step 6•4].

Then, by using the inputted sample information [step 6•1] and either the crystal information retrieved from the existing crystal information database [step 6•3 Yes] or the crystal information from the newly prepared crystal information database [step 6•4], the crystal sample data such as the coordinates and the structure factors to all the reciprocal lattice points in the limiting sphere of the crystal sample are calculated [step 6•5]. That is, the orientation of the crystal sample is determined by the sample information, and the crystal sample data of the crystal sample in this orientation are obtained with the crystal information.

The calculation of the coordinates and the structure factors to the reciprocal lattice points carried out here is well known, the coordinates are obtained by using, for example, a well-known UB matrix, and the structure factors are obtained from the space group, the lattice constants, the atomic position, and the temperature factor.

Figure 7:
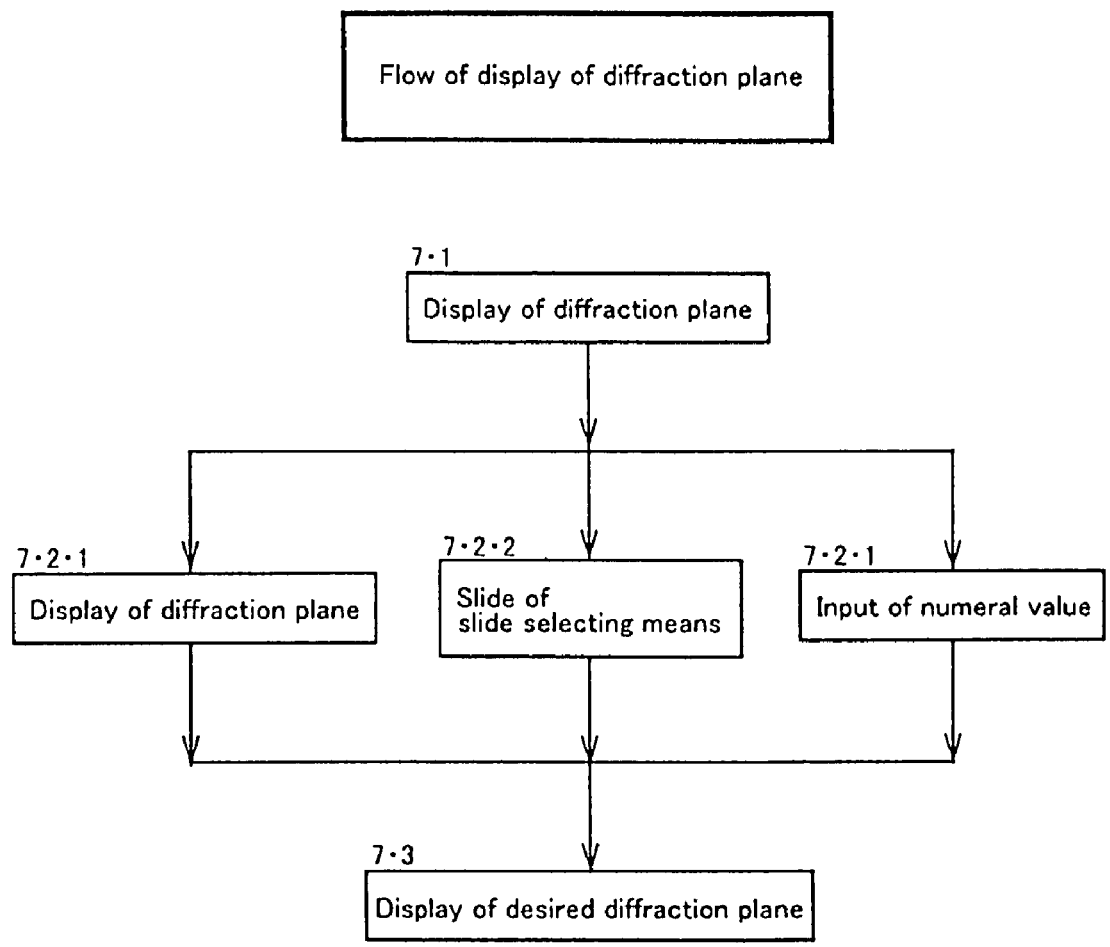
FIG. 7 shows an operational flow of a diffraction plane display.

Flow of Display of Diffraction Plane [FIG. 5, step 5•2; FIG. 7]

Next, based on the coordinates of all the reciprocal lattice points in the crystal sample data calculated by the foregoing flow of the crystal sample data preparation, as exemplified in FIG. 2, the section where reciprocal lattice points 3 in the limiting sphere rotating in synchronizing with the rotation of a crystal intersect a diffraction plane, together with a limiting sphere section 2, is displayed on the computer screen [step 5•2]. The rotation of a crystal may be considered the same as the rotation of crystal orientation.

More specifically (see FIG. 7), the reciprocal lattice points 3 on the diffraction plane calculated (determined) in accordance with the rotation of a crystal sample 1, that is, calculated by using the rotation angles, the χ angle and the ϕ angles of the crystal sample 1, as well as the limiting sphere section 2 surrounding the reciprocal lattice points are displayed [step 7.1]. The calculation (determination) of the reciprocal lattice points 3 on the diffraction plane using the χ angle and the ϕ angle as the orientation angles of a crystal is well known. The diffraction plane is a plane on which both an incident vector and an outgoing reflection vector are placed.

Figure 1:
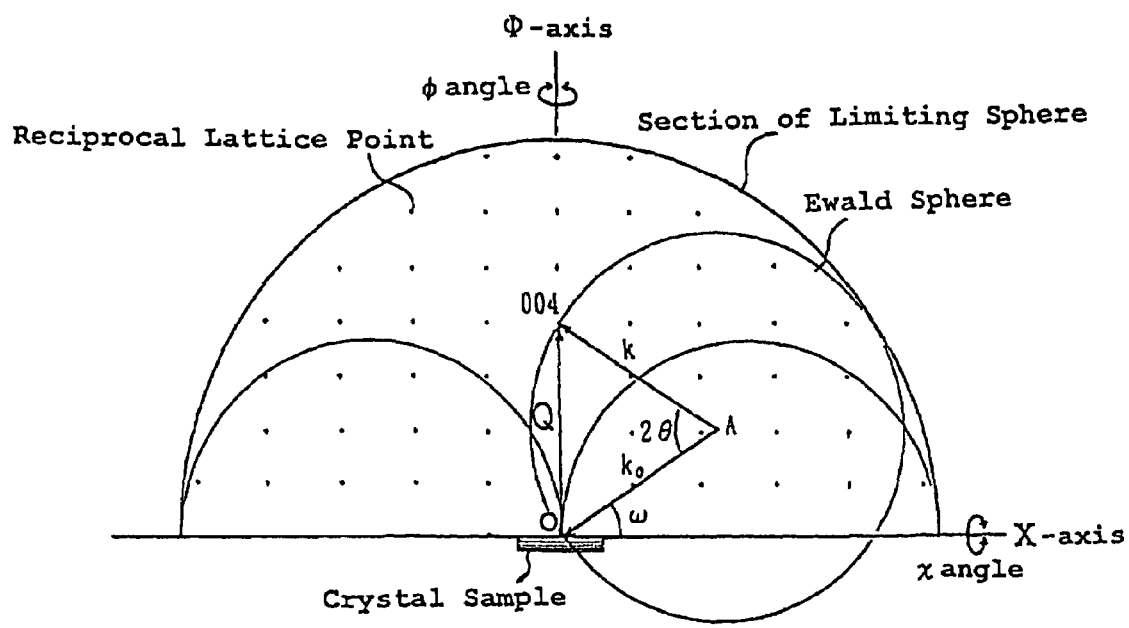
FIG. 1 is a conceptual view exemplifying a limiting sphere and an Ewald sphere of a crystal sample.

Further, this limiting sphere section 2 is calculated on the basis of the crystal sample 1 rotated correspondingly to the moving direction of the pointer on the computer screen [step 7.2•1]. In this case, more specifically, when the pointer is moved, the crystal sample 1 is rotated along the X-axis and the Φ-axis (see FIG. 1). Thus, the χ angle and the φ angle, the rotation angles along the X-axis and the Φ-axis, are changed in accordance with the moving direction and the moving amount of the pointer, and the reciprocal lattice rotates in accordance with the change of the χ angle and the φ angle. In this rotation, the reciprocal lattice points 3 on the diffraction plane in the limiting sphere section 2 are displayed. In other words, among all the previously calculated reciprocal lattice points 3 included in the crystal sample 1, the reciprocal lattice points 3 placed on the diffraction plane by the rotated reciprocal lattice are always displayed in the limiting sphere section 2 during the rotation.

Hence, for example, if the movement of the pointer is stopped when the desired reciprocal lattice point 3 appears on the screen, the diffraction plane including the reciprocal lattice point 3 can be displayed [step 7•3].

As described above, in the diffraction condition simulation device of this invention, the limiting sphere section 2, together with the diffraction plane including the reciprocal lattice points 3, (hereinafter, it is assumed that the diffraction plane is placed in the limiting sphere section) is rotatably displayed in accordance with the rotation of the crystal sample, and the reciprocal lattice of the crystal sample 1 can be rotated along the movement of the pointer, and further, the foregoing display is always made during the rotation. Therefore, the diffraction plane containing a desired reciprocal lattice point 3 can be quickly and easily displayed.

Incidentally, the movement of the pointer is generally operated by external operating means such as a mouse or an arrow key of a keyboard. It is preferable that rotation display by the pointer is made effective in only a case where, for example, on the computer screen exemplified in FIG. 2, the pointer is positioned in a limiting sphere section display window 21 displaying the limiting sphere section 2.

The rotation of the reciprocal lattice of the crystal sample 1 may be carried out through, for example, a χ angle slide selecting means 41 and a φ angle slide selecting means 42 displayed on the computer screen exemplified in FIG. 2 [step 7•2•2].

These slide selecting means 41 and 42 are slidable by devices such as the pointer or right and left arrow keys of the keyboard, and an arbitrary numerical value of the χ angle and the φ angle of the crystal sample 1 can be selected by the slide. Thus, the χ angle and the φ angle are continuously changed correspondingly to the slide of the pointer or arrow key, and the reciprocal lattice is continuously rotated. Of course, similarly to the rotation display by the pointer, the reciprocal lattice points 3 are also always displayed, and the diffraction plane containing the desired reciprocal lattice point 3 can be quickly and easily displayed together with the limiting sphere section 2 [step 7•3].

In the example shown in FIG. 2, a χ angle numerical value display portion 51 and a φ angle numerical value display portion 52 are provided in the vicinity of the χ angle slide selection means 41 and in the vicinity of the φ angle slide selection means 42, respectively, and the χ angle and the φ angle slide-selected by the respective slide selection means 41 and 42 are displayed on the χ angle numerical value display portion 51 and the φ angle numerical value display portion 52, respectively.

As the rotation of the reciprocal lattice occurs by the movement of the pointer, the numerical values of the χ angle and the φ angle accompanied by the rotation can be displayed on the χ angle numerical value display portion 51 and the φ angle numerical value display portion 52, respectively.

By such numerical value display of each angle, it is possible to know easily in what orientation of the crystal sample 1 the diffraction plane containing the desired reciprocal lattice point 3 is displayed.

Further, numerical values of the χ angle and the φ angle may be inputted by a keyboard or ten-key, and for example, such numerical values can be directly inputted into the χ angle numerical value display portion 51 and the φ angle numerical value display portion 52, respectively [step 7•2•3]. Then, in accordance with the inputted numerical values, the reciprocal lattice point 3 in the diffraction plane is changed [step 7•3].

In addition, it is desirable that each of the reciprocal lattice points 3 in the diffraction plane is displayed so that the difference in magnitude of the structure factor is expressed on the basis of the structure factor previously calculated as crystal sample data. For example, such a difference may be displayed by changing the color of each of the reciprocal lattice points 3 according to the magnitude of the structure factor.

When any one of the reciprocal lattice points 3 displayed in the diffraction plane is chosen arbitrarily, the structure factor by selecting a "F order" button located just above the display portion 62 and the Miller indices hkl of the reciprocal lattice point 3 chosen are displayed in a structure factor display 61 provided on the computer screen as shown in FIG. 2 as an example.

All the reciprocal lattice points 3 included in the crystal sample 1 may be arranged and displayed in order of the structure factor. In this case, for example, as shown in FIG. 2, in a reciprocal lattice point permutation display portion 62 provided on the computer screen, the Miller indices hkl and the structure factor of each reciprocal lattice point 3 are displayed in order of the magnitude of the structure factor and can be scroll-retrieved in the order of the structure factor by scroll means 63 provided in the vicinity of the reciprocal lattice permutation display portion 62.

Moreover, for example, when any one of the Miller indices hkl of the reciprocal lattice point 3 displayed on the reciprocal lattice point permutation display portion 62 is selected and is specified by pressing a set button 64, the diffraction plane containing the reciprocal lattice point 3 of the selected Miller indices hkl can also be displayed.

As described above, according to the present invention, the reciprocal lattice points 3 are displayed such that the structure factor of each is displayed, and/or they are displayed such that the difference in the magnitude of the structure factor appears, and/or they are arranged and displayed in order of the magnitude of the structure factors. Consequently, the intensity of Bragg reflection can be extremely easily estimated for any of the reciprocal lattice points 3.

Figure 8:
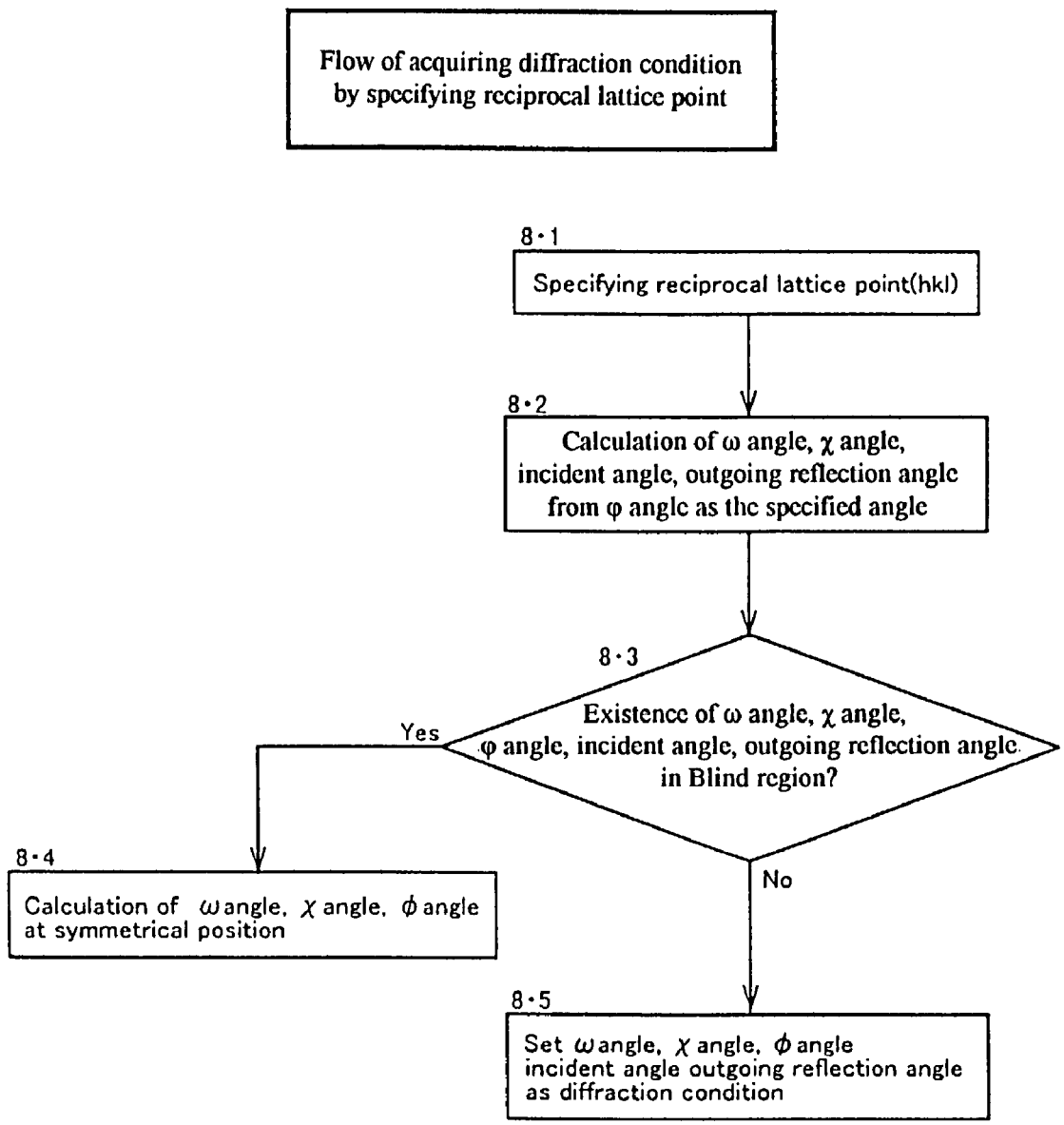
FIG. 8 shows an operational flow to specify a diffraction point.

Flow of Setting Up of Diffraction Condition by Specifying Reciprocal Lattice Point [FIG. 5 step, 5•3; FIG. 8]

In the diffraction condition simulation device of this invention, the diffraction plane containing reciprocal lattice points 3 is displayed on the computer screen as described above, so that each reciprocal lattice point 3 for the crystal sample 1 can be recognized, that is, the Bragg reflection can be recognized and further, a diffraction condition of the Bragg reflection at a reciprocal lattice point 3 can be obtained by specifying the desired reciprocal lattice point 3 among all the reciprocal lattice points 3 displayed.

More specifically, along the flow diagram shown in FIG. 8 as an example, first, a desired reciprocal lattice point 3 is specified [step 8•1]. This may be done by, for example, moving the pointer to the reciprocal lattice point 3 displayed on the screen and pressing the left button of mouse or the determination key of keyboard. If the desired reciprocal lattice point 3 is not being displayed on the screen, it may be specified by selecting, as described above, its Miller indices hkl from the reciprocal lattice point permutation display portion 61. Of course, as the Miller indices hkl are selected, the diffraction plane containing the desired reciprocal lattice point 3 is displayed on the screen.

When the desired reciprocal lattice point 3 is specified, the $\chi$ angle and the $\chi$ angle as the other orientation angles, the incident angle of X rays or particle beam (X rays in this embodiment) to the crystal sample 1, and the outgoing angle from the crystal sample 1 are calculated, using the $\phi$ angle as the specified orientation angle of the crystal sample 1 [step 8•2]. This calculation is carried out by using a well-known equation.

Next, it is evaluated whether the $\omega$ angle, the $\phi$ angle, the $\chi$ angle, the incident angle, and the outgoing angle exist in a Blind region 22 where the actual measurement of the Bragg reflection can not be made [step 8•3]. This Blind region 22 is, as exemplified in FIG. 2, indicated in the limiting sphere section 2 by two small semicircles each having a diameter equal to the radius of the limiting sphere section 2.

In the case where they do not exist in the Blind region 22, the $\omega$ angle, the $\phi$ angle, the $\chi$ angle, the incident angle, and the outgoing angle are directly set as diffraction conditions [step 8•5].

In the case where they exist in the Blind region 22, the $\omega$ angle, the $\chi$ angle, and the $\phi$ angle are newly calculated in a symmetrical diffraction conditions where the incident angle is equal to the outgoing angle [step 8•4], and these angles are set as the diffraction conditions [step 8•5].

In this way, diffraction conditions of the Bragg reflection to the arbitrarily specified reciprocal lattice point 3 can be obtained. On the computer screen, as shown in FIG. 3 as an example, the Bragg reflection to the specified reciprocal lattice point 3 is displayed. In the example shown in FIG. 3, the reciprocal lattice point 3 of 205 is specified, and as the diffraction condition which satisfies the Bragg reflection to the reciprocal lattice point 3, $\omega$ angle=85.060°, $\phi$ angle=92.110°, $\chi$ angle=33.55°, incident angle=56.13°, and outgoing angle=41.36° are obtained, and in addition, an incident line 72 of the X rays, an outgoing reflection line 73, and a reciprocal lattice vector 74 are displayed in the diffraction plane together with a Ewald sphere 71.

Additionally, the reciprocal lattice points 3 may be arranged and displayed on the reciprocal lattice permutation display portion 62 in the order of the magnitude of diffraction angle 2θ of the Bragg reflection.

Furthermore, for example, it may be designed such that when the reciprocal lattice point 3 or its vicinity is clicked by the right button of a mouse, a structure factor and 2θ angle are displayed in the vicinity of the reciprocal lattice points.

Figure 9:
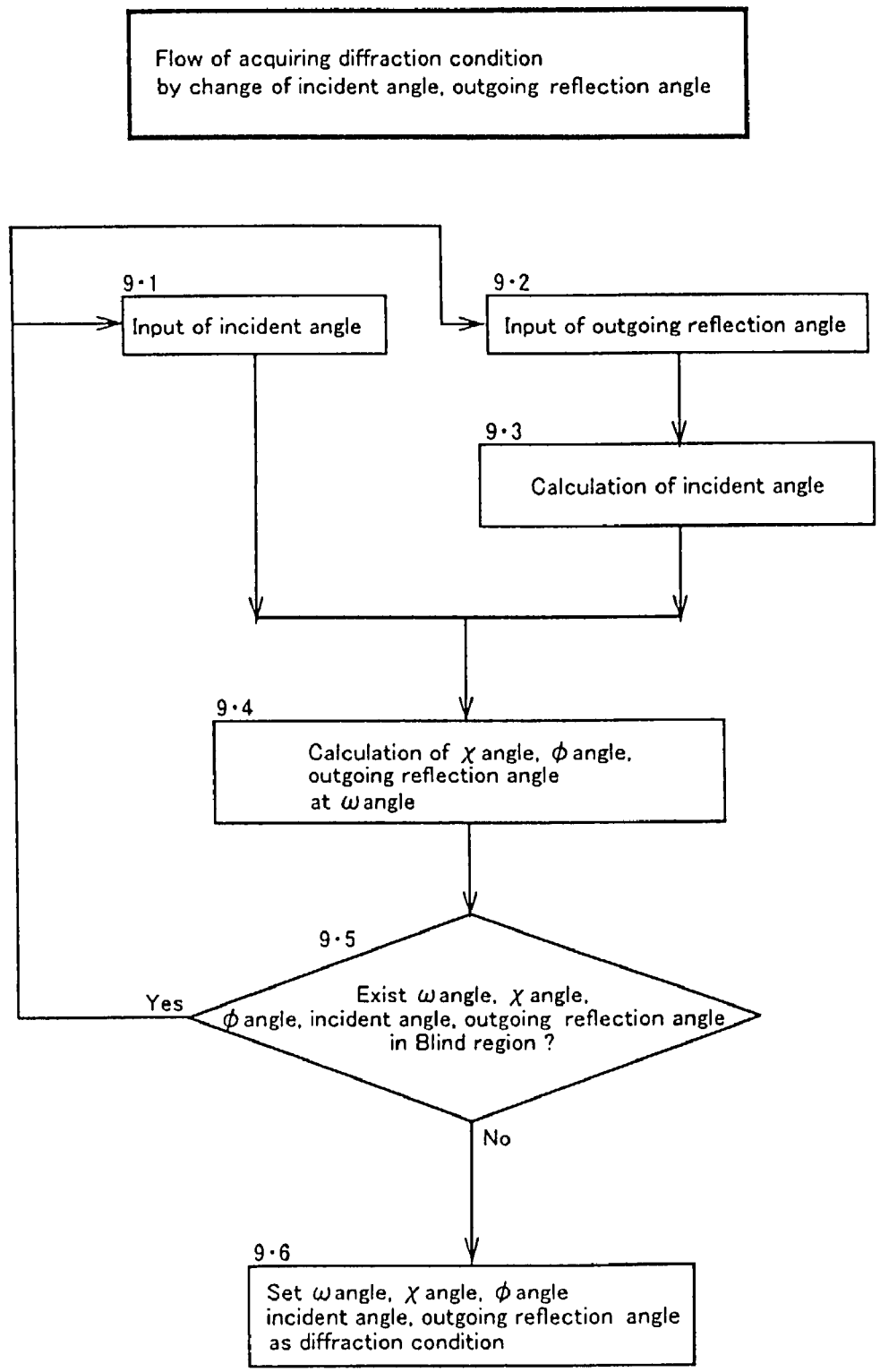
FIG. 9 shows an operational flow of renewal of an incident angle, outgoing angle.

Flow of Acquiring Diffraction Conditions by Change of Incident Angle and Outgoing Angle [FIG. 5, step 6•4; FIG. 9]

In the diffraction condition simulation device of this invention, further, a diffraction condition can be changed arbitrarily (renewal of diffraction condition), thereby obtaining and displaying the Bragg reflection which satisfies new diffraction condition, that is, the reciprocal lattice point. This renewal of the diffraction condition maybe carried out [step 5•5 Yes] as described below.

Firstly, at least one of the incident angle or the outgoing angle among the diffraction conditions is changed, thereby acquiring a new diffraction condition.

As shown in the flow diagram of FIG. 9, in a case where the incident angle is newly inputted [step 9•1], the $\omega$ angle, the $\chi$ angle, $\phi$ angle, and outgoing angle are calculated [step 9•4].

In a case where the outgoing angle is newly inputted [step 9•2], after calculating the incident angle by the outgoing angle inputted [step 9•3], the $\omega$ angle, $\chi$ angle, $\phi$ angle, and outgoing angle are calculated [step 9•4].

Then it is judged whether the obtained $\omega$ angle, $\chi$ angle, $\phi$ angle, incident angle, and outgoing angle exist in the Blind region 22, and if they exist in the Blind region 22, the input of the incident angle or outgoing angle is again carried out [step 9•5 Yes], and if they do not exist in the Blind region 22 [step 9•5 No], the $\omega$ angle, $\chi$ angle, $\phi$ angle, incident angle, or outgoing angle are set as new diffraction conditions [step 9•6].

Here, the incident angle and the outgoing angle can be changed by, for example, as shown in FIG. 3, dragging the incident line 72 or the outgoing reflection line 73 displayed in the diffraction plane on the computer screen by a mouse through a pointer.

Selection of a new incident angle and outgoing angle can also be easily and continuously carried out by sliding the incident angle slide selecting means 43 and the outgoing angle slide selecting means 44 which are provided on the computer screen through pointer movement by mouse operation, an arrow key or the like.

Further, angles can be directly inputted in an incident angle numerical value display portion 53 and also in an outgoing angle numerical value display portion 54. These display portion 53 and 54, disposed in the vicinities of the incident angle slide selecting means 43 and the outgoing angle slide selecting means 44, respectively, display the numerical value of the incident angle and the numerical value of the outgoing angle.

Figure 10:
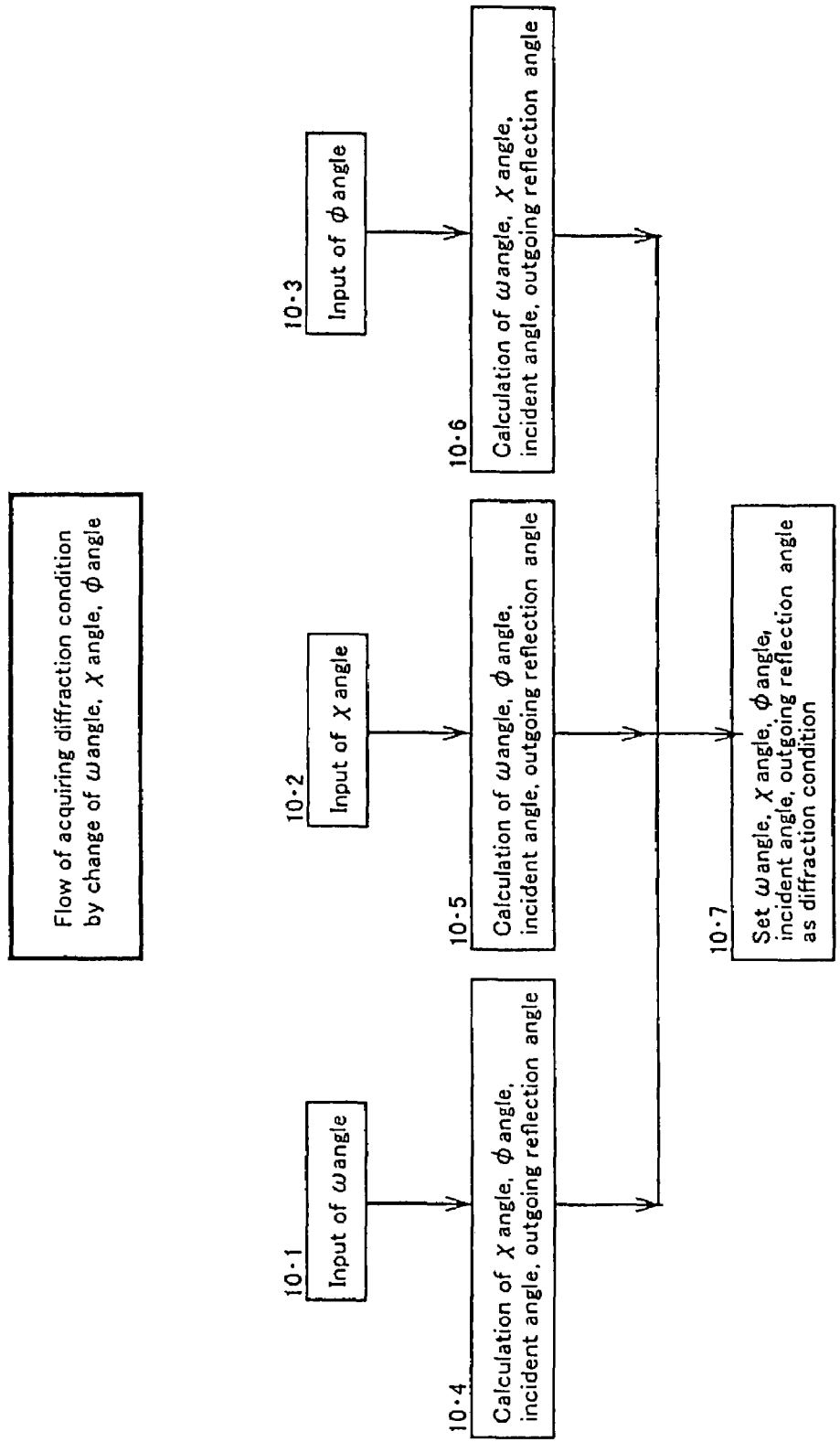
FIG. 10 shows an operational flow of renewal of ω angle and Φ angle.

Flow of Acquiring Diffraction Conditions by Chance of $\omega$ Angle, $\chi$ angle, and $\phi$ Angle [FIG. 5, step 5•5; FIG. 10]

Here, instead of changing the incident angle or the outgoing angle as described above, at least one of the $\omega$ angle, $\chi$ angle, and $\phi$ angle which define the diffraction conditions maybe changed, thereby a new diffraction condition is acquired.

As shown in the flow of FIG. 10 as an example, when the $\omega$ angle is inputted [step 10•1], the $\chi$ angle, $\phi$ angle, incident angle, and outgoing angle are calculated from the inputted $\omega$ angle [step 10•4]. When the $\chi$ angle is inputted [step 10•2], the $\omega$ angle, $\phi$ angle, incident angle, and outgoing angle are calculated from the inputted $\chi$ angle [step 10•5]. When the angle is inputted [step 10•3], the $\omega$ angle, $\chi$ angle, incident angle, and outgoing angle are calculated from the input $\phi$ angle [step 10•6]. Then each of these angles is set as a new diffraction condition [step 10•7].

The input of these $\omega$ angle, $\chi$ angle, and $\phi$ angle can be made by selection with a slide of the $\omega$ angle slide selecting means 45, the $\chi$ angle slide selecting means 41, and the $\phi$ angle slide selecting means 42, or by the direct input of a numerical value to the $\omega$ angle numerical value display portion 55, the $\chi$ angle numerical value display portion 51, and the $\phi$ angle numerical value display portion 52.

Each of the inputted angles and calculated angles is set as a new diffraction condition.

As described above, each time when the diffraction condition is renewed, the Bragg reflection of the reciprocal lattice point 3 satisfying a new diffraction condition is displayed within the limiting sphere section 2.

Enlargement Display [FIG. 5, step 5•6]

Moreover, in the diffraction condition simulation device of this invention, it is preferable that the reciprocal lattice point can be displayed with enlargement.

For example, in this enlargement display [step 5•6 Yes], as exemplified in FIG. 4, a region of a diffraction including reciprocal lattice point 3 is selected by a mouse operation or the like through a pointer on the screen, and this region, called an enlargement region 81, can be enlarged with an enlargement rate $\sigma_2$ of default previously set by pressing an enlargement display button 65 (indicated as "magnify" in FIG. 4) provided on the screen. The enlargement rate $\sigma_2$ can be changed by inputting a desired enlargement rate.

In the example shown in FIG. 4, the reciprocal lattice point 3=205 is specified, and the enlargement region 81 which is a peripheral region including the reciprocal lattice 3=205 is enlarged in the enlargement display frame 82 as a separate frame, where the diffraction condition satisfying the Bragg reflection for the reciprocal lattice point 3=205 is given as χ angle=33.55°, φ angle=−92.11°, incident angle=56.13°, and outgoing angle=41.36°.

By such enlargement display, the resolution between Bragg reflections locating very close by each other can be improved, thereby improving the quality of display so as to be able to see the profile of reflection and crystal structure evaluation can be made easier.

Inversion display [FIG. 5. step 5•6]

In addition, the direction of the incident angle and outgoing angle may be freely inverted. This inversion of the direction can be arbitrarily and easily inverted [step 5•7 Yes] by, for example, pressing a display inversion button 66 provided on the computer screen.

Crystal Orientation Simulation [FIG. 5. step 5•7]

Figure 11:
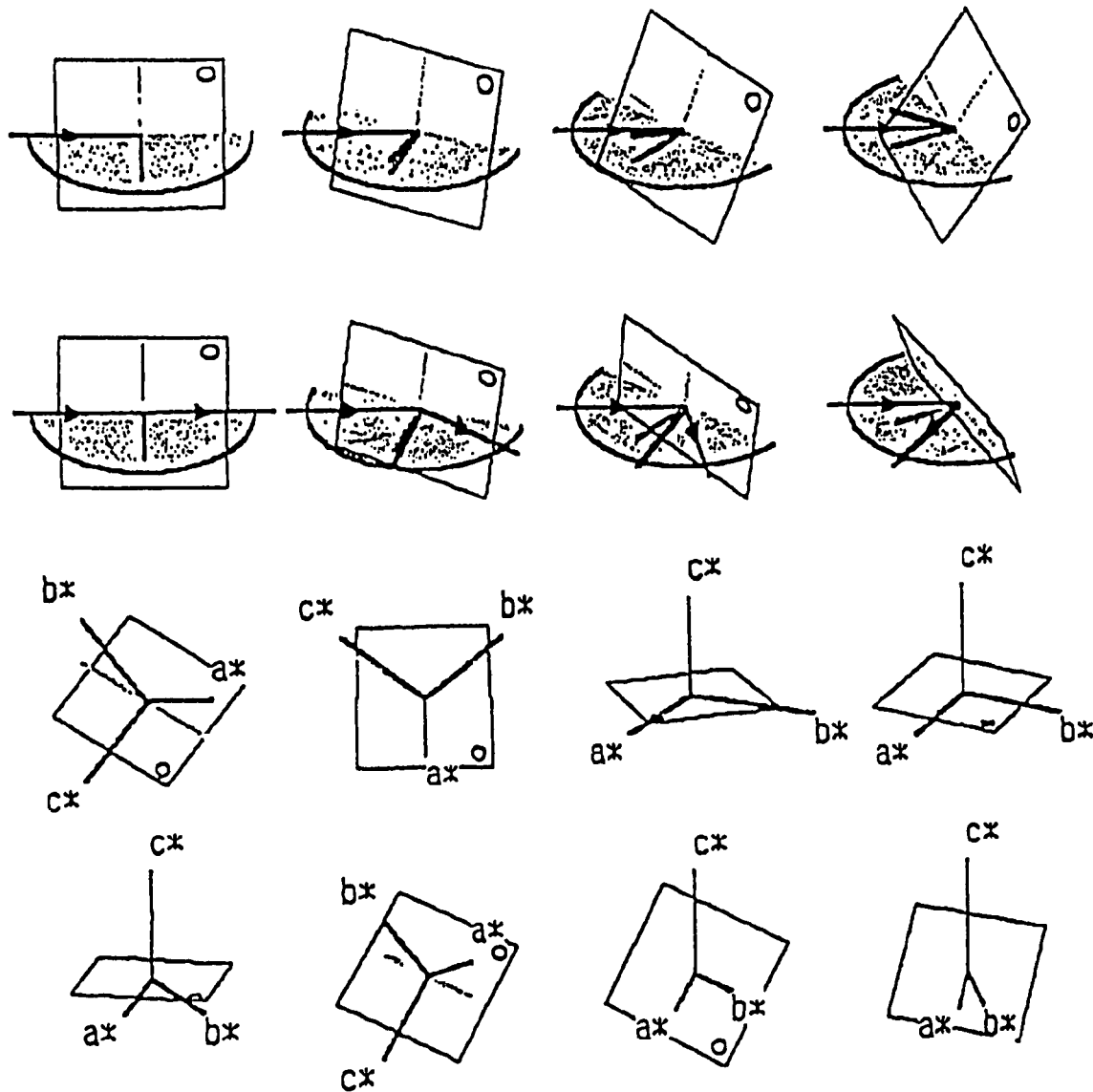
FIG. 11 is a view showing an example of crystal orientation drawings on a computer screen by a diffraction condition simulation device of the present invention.

Furthermore, when the diffraction conditions are renewed as described above, the ω angle, χ angle,. φ angle, incident angle, and outgoing angle as new diffraction conditions are set for a crystal orientation, and the crystal orientation is drawn on the screen, for example, as shown in FIG. 11. Further, the incident direction and outgoing direction of X rays or particle beams can also be displayed [step. 5•2].

Movement of Goniometer [FIG. 5 step 5•8]

In a case where the diffraction condition simulation device of this invention is connected with a diffraction measurement system for measuring the Bragg reflection of X rays or particle beams by a crystal sample, the simulated diffraction conditions where the Bragg reflection occurs, that is, the values of the χ angle and φ angle of the crystal sample, and the incident angle (or ω angle) and outgoing angle (or diffraction angle 2θ) of X rays or particle beams can be transmitted to the diffraction measurement system by pressing a four-axis angle transmission button 67 displayed on the screen, and actual measurement of the diffraction beam satisfying the diffraction conditions, that is, the Bragg reflection can be measured in the diffraction measurement system.

Figure 12:
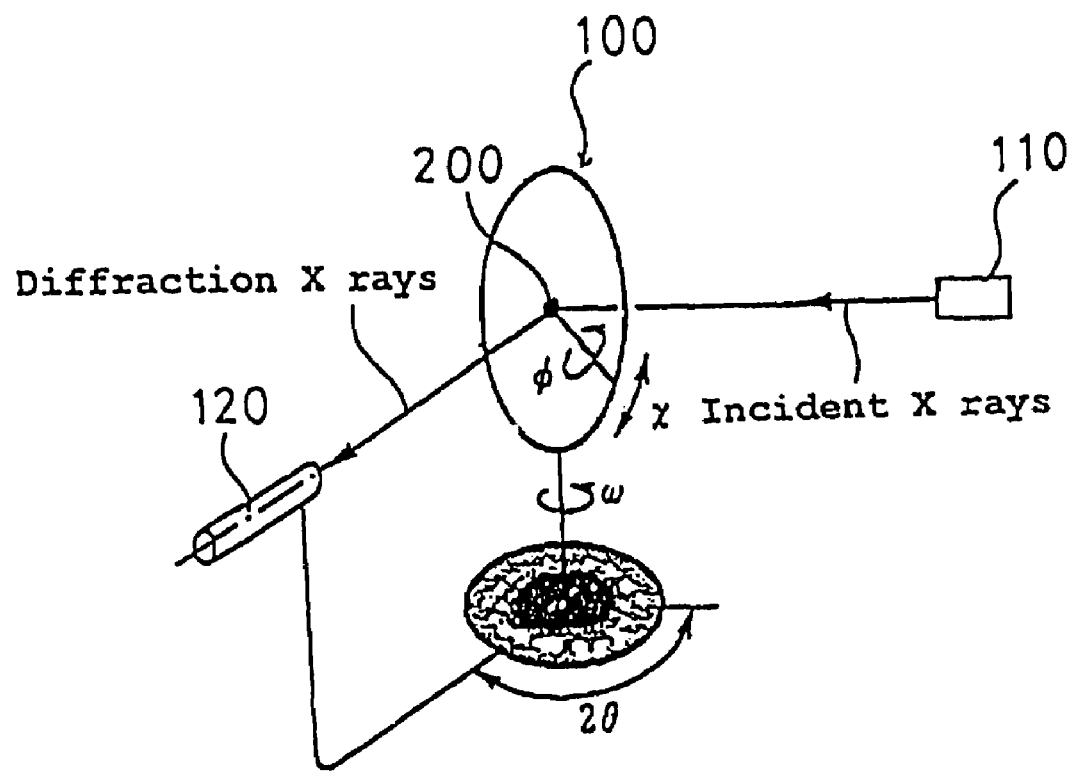
FIG. 12 schematically illustrates an example of a diffractometer comprising a four-axis goniometer, an X-ray source, and a detector.
Figure 13:
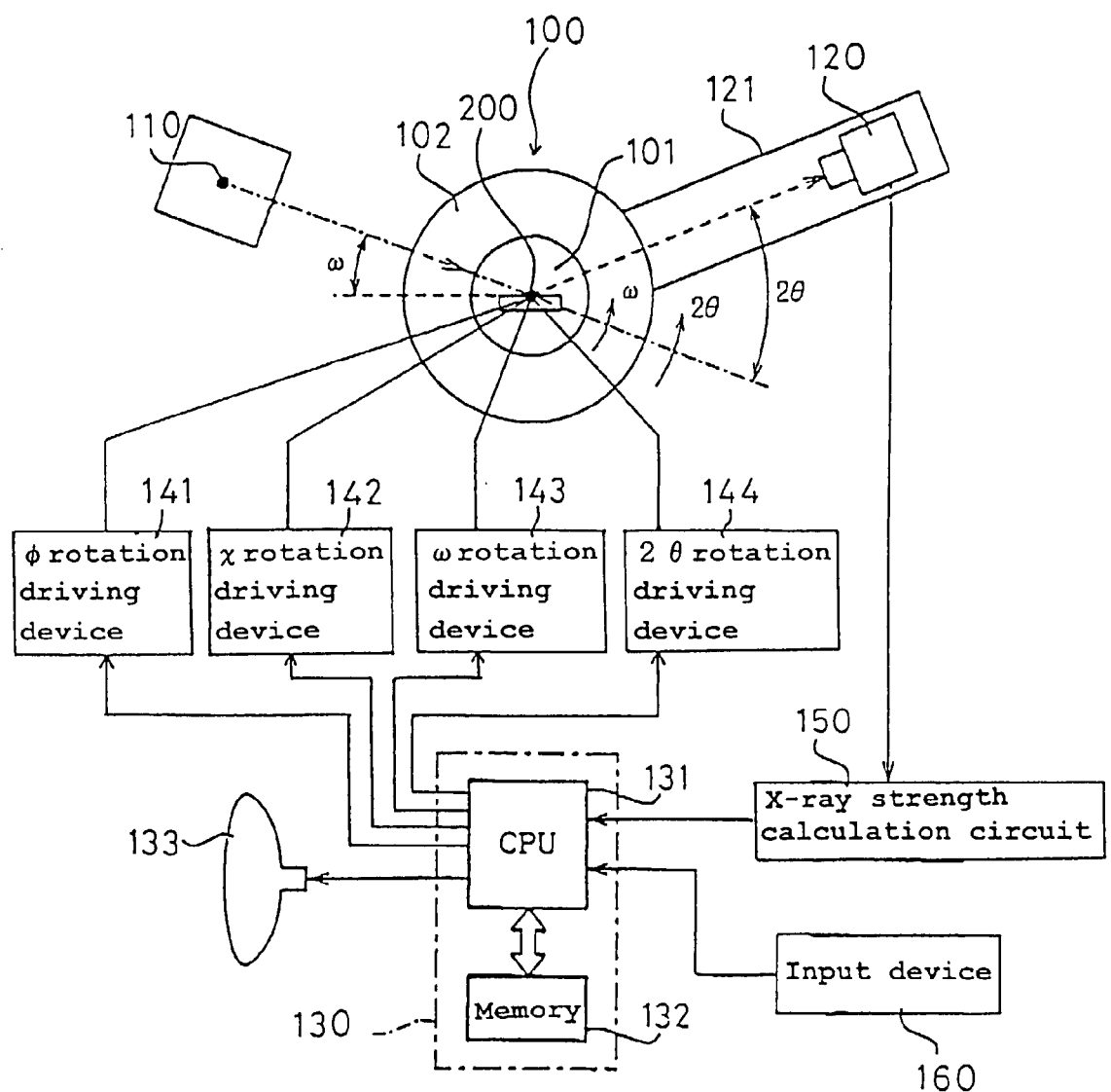
FIG. 13 schematically illustrates one embodiment of a diffraction measurement system and a crystal analysis system of the present invention.

FIGS. 12 and 13 show an example of the diffraction measurement system of this invention.

The diffraction measurement system of this invention includes, for example, a four-axis goniometer 100 provided with four rotating axes, an X-ray source 110 for producing X rays, a detector 120 for detecting diffraction beams, such as an X-ray counter, a controlling computer 130 having a CPU 131, a memory 132, and a CRT display (display device) 133 , and a φ rotation driving device 141, a χ rotation driving device 142, an ω rotation driving device 143 and a 2θ rotation driving device 144 for driving the respective rotation axes of the four-axis goniometer 100. In addition, 101 is an ω rotation support, 102 is a 2θ rotation support, 160 is a input device for input to the controlling computer 130.

Although the structure itself for diffraction measurement is well known, the system has a feature that the simulated diffraction conditions obtained by the diffraction condition simulation device of this invention are used, and the operation and the like are controlled by the controlling computer 130 in accordance with the simulated diffraction conditions. In FIG. 13, the diffraction condition simulation device is stored as software in the memory 132 of the controlling computer 130.

More specifically, when the φ, χ, ω and 2θ angles as diffraction conditions obtained by the diffraction condition simulation device of this invention are given to the CPU 131 of the controlling computer 130, the CPU 131 controls each of the φ rotation driving device 141, the χ rotation driving device 142, the ω rotation driving device 143 and the 2θ rotation driving device 144, thereby rotating each axis of the four-axis goniometer 100 so that each of an actual φ, χ, ω, and 2θ angles becomes equal to the value of its simulated angle (same orientation).

Then, for example, the detector 120 disposed on a detector arm 121 scans a definite space automatically and detects a main reciprocal lattice point, that is, the Bragg reflection, and an X-ray intensity calculation circuit 150 measures the value of its intensity on an equatorial plane consisting of incident X rays, a crystal sample, and the detector 120.

In this diffraction measurement system, when the crystal is rotated to satisfy the diffraction conditions, although there are three freedoms of ω, χ, and φ angle, the number of freedoms necessary for setting a diffraction point is two. That is, since one surplus freedom exists, it is possible to make measurements by rotating a specific reflection around its scattering vector, that is, along a normal of a diffracting crystal plane. Thus, multiple reflections and the like can be detected.

Figure 14:
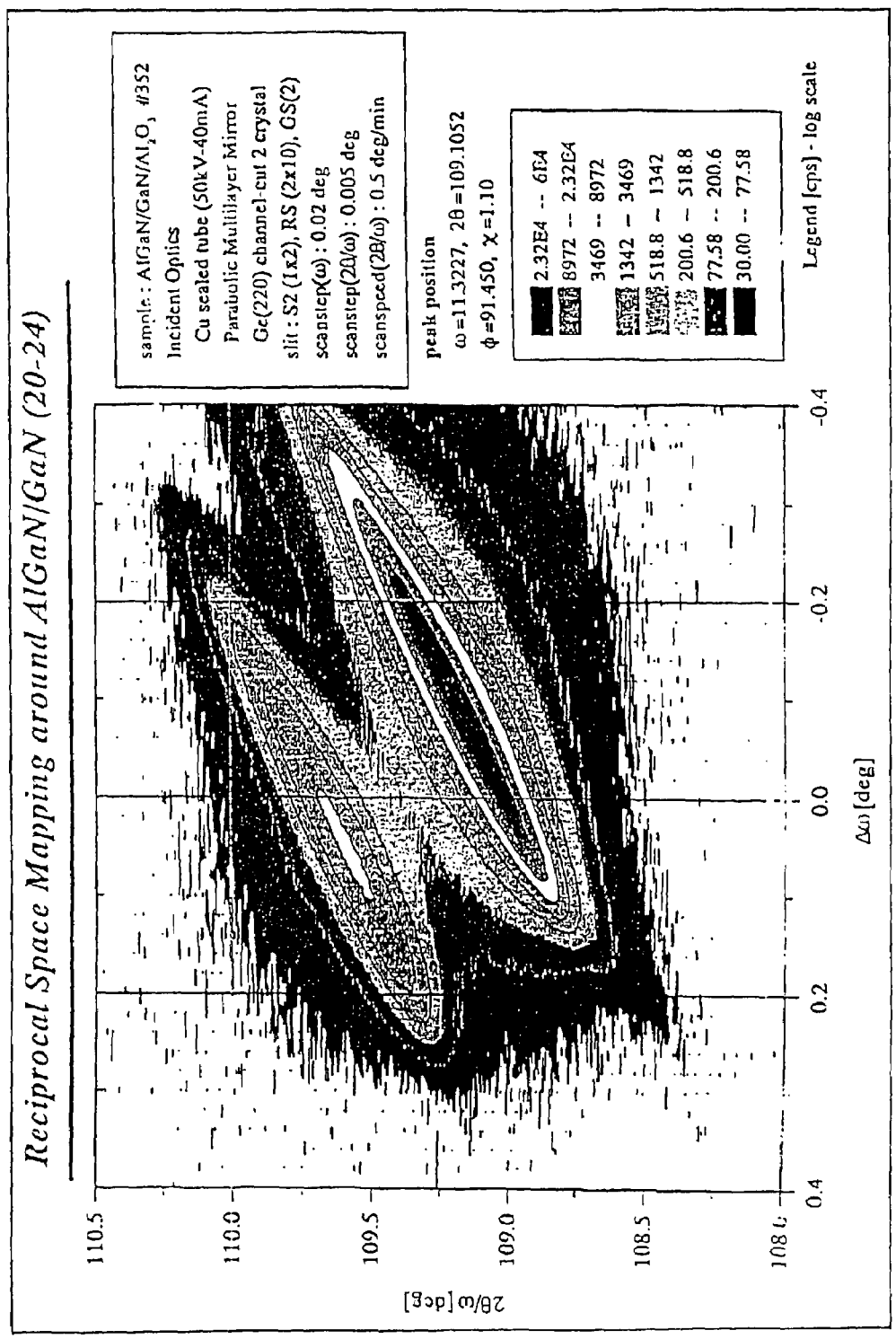
FIG. 14 is a view showing an example of a reciprocal lattice map measured by a diffraction measurement system of the present invention.

As described above, the diffraction measurement system of this invention uses diffraction conditions simulated by the diffraction condition simulation device of this invention, and can actually measure the Bragg reflection satisfying the diffraction conditions. It is needless to say that in an actual measurement, for example, it is possible to measure a region in the vicinity of a Bragg reflection in a mesh-like manner. The mesh-like measurement itself of the region in the vicinity of a Bragg reflection is well known, and its measurement result is generally called a reciprocal lattice map. FIG. 14 shows an example of the reciprocal lattice map measured by the diffraction measurement system of this invention. In the example shown in FIG. 14, an AlGaN/GaN thin film is used as a crystal sample.

Since it is sufficient if the diffraction simulation device can give simulated diffraction conditions to the diffraction measurement system, more specifically, to the controlling computer 130 of the diffraction measurement system, other than a case where the diffraction simulation device is included as software in the controlling computer 130, it may be included in a separate computer or it may be made as a separate device. The diffraction simulation device made as a separate computer or separate device is connected to the controlling computer 130 of the diffraction measurement system through connecting means or the like, and the simulated diffraction conditions are transmitted to the controlling computer 130.

Further, the system exemplified in FIG. 13 can also be made a crystal analysis system of this invention for analyzing a crystal sample 200 by using the measured Bragg reflection. That is, by providing the controlling computer 130 with analyzing means, the structure analysis, evaluation and the like of the crystal sample can be made with the use of the measured Bragg reflection. For example, an analyzing program as such analyzing means can be stored in the memory 132 of the controlling computer 130.

Of course, the crystal analysis system may be provided as a separate body from the diffraction measurement system, and in this case, the Bragg reflection measured by the diffraction measurement system is transmitted to the crystal analysis system through connection means and the like.

Although the diffraction measurement system and the crystal analysis system of this invention are provided with a well-known four-circle goniometer, it is needless to say that the goniometer is not limited to the four-circle type, but a goniometer with five, six, or more axes can be applied to the system, using the diffraction conditions, that is, the $\phi$, $\chi$, $\omega$, and $2\theta$ angles, simulated by the diffraction condition simulation device as basic angles.

Although X rays are used as incident beams in the above embodiment, it is needless to say that excellent simulation of a diffraction phenomenon can be made also for particle beams such as neutral beams or electron beams, similarly to the case of the X rays.

The crystal sample as the object of the diffraction condition simulation device, the diffraction measurement system, and the crystal analysis system of this invention includes any crystallized sample, for which a reciprocal lattice can be expressed.

As described above in detail, by the diffraction condition simulation device of this invention, the diffraction plane containing reciprocal lattice points is displayed in accordance with continuous rotation of the reciprocal lattice, and the structure factor of each of the reciprocal lattice points is also displayed, so that simulation of a desired Bragg reflection can be quickly and easily calculated and displayed. It is also possible to distinguish the diffraction intensity and to differentiate a general reflection from a forbidden reflection, and in addition, it is possible to arbitrarily specify the $\omega$, $\chi$, and $\phi$ angles which determine the orientation of a crystal sample, the incident angle and the outgoing angle of X rays or particle beams and to control and set them as diffraction conditions. Accordingly, display of reciprocal lattices expressing various Bragg reflections can be made, and excellent evaluation and analysis of crystal structure can be realized.

Furthermore, by the diffraction measurement system and the crystal analysis system of this invention, it becomes possible, with the use of diffraction conditions obtained by the diffraction condition simulation device of this invention, to extremely easily make actual measurement of a thin film, for example, based on an asymmetrical reflection in which a diffraction vector from the origin to a reciprocal lattice point does not coincide with a sample normal, or based on the grading incidence of X rays or particle beams to the crystal sample surface, and also to analyze the crystal structure of a sample using the obtained result, and so on.

Second Embodiment

Hereinafter, we explain, with more details, how the device of the invention obtains a Bragg reflection condition.

Firstly, the CPU of the device stores lattice constants and crystal orientations of a crystal constituting the crystal sample in the memory. The lattice constants and crystal orientations are inputted to the CPU by the operator of the device. The device may have a database having lattice constants of various crystal samples as crystal information and may retrieve the lattice constants of the crystal of the desired crystal sample.

Secondly, the CPU performs calculation of a crystal orientation matrix U of the UB matrix by using the crystal orientations of the crystal stored in the above memory. This crystal orientation matrix U represents an orientation of the crystal.

Thirdly, the CPU performs calculation of a crystal lattice matrix B of the UB matrix by using the lattice constants of the crystal stored in the above memory. This crystal lattice matrix B represents a lattice of the crystal and an initial orientation of the crystal.

Finally, the CPU performs calculation of a rotation matrix R, which represents rotation angles of rotation axes of a diffraction measurement device, by using the orientation matrix U and the crystal lattice matrix B calculated as above and also a value of one of the rotation angles designated by the operator. The operator can designate any one of the rotation angles by operating any one of the slide selecting means or inputting a numerical value of the desired rotation angle into the corresponding numerical value display portion on the computer screen, for example. Thus obtained rotation matrix R of rotation angles satisfies a diffraction condition of a Bragg reflection designated by the operator.

Accordingly, when one of the rotation angles is specified by the operator, all the other rotation angles which satisfy a desired Bragg reflection condition can be obtained. In other words, the operator of the device of the invention can obtain any Bragg reflection conditions of any desired Bragg reflection only by designating one rotation angle on the computer screen.

In the above invention, matrix elements constituting the UB matrix and the rotation matrix R, which are calculated by the CPU, vary according to the type of the diffraction measurement device. For example, the matrix elements for the 3-circle goniometer differ from those for the 4-circle goniometer. Also, even for the same numbered circle goniometer, the matrix elements differ with arrangement or mechanism of the axes. Thus, the UB matrix and the rotation matrix R must be established according to the diffraction measurement device.

ATX-E Goniometer

Here, we explain about the UB matrix and the rotation matrix R for the ATX-E goniometer which is an in-plane diffractometer by this applicant.

Figure 15:
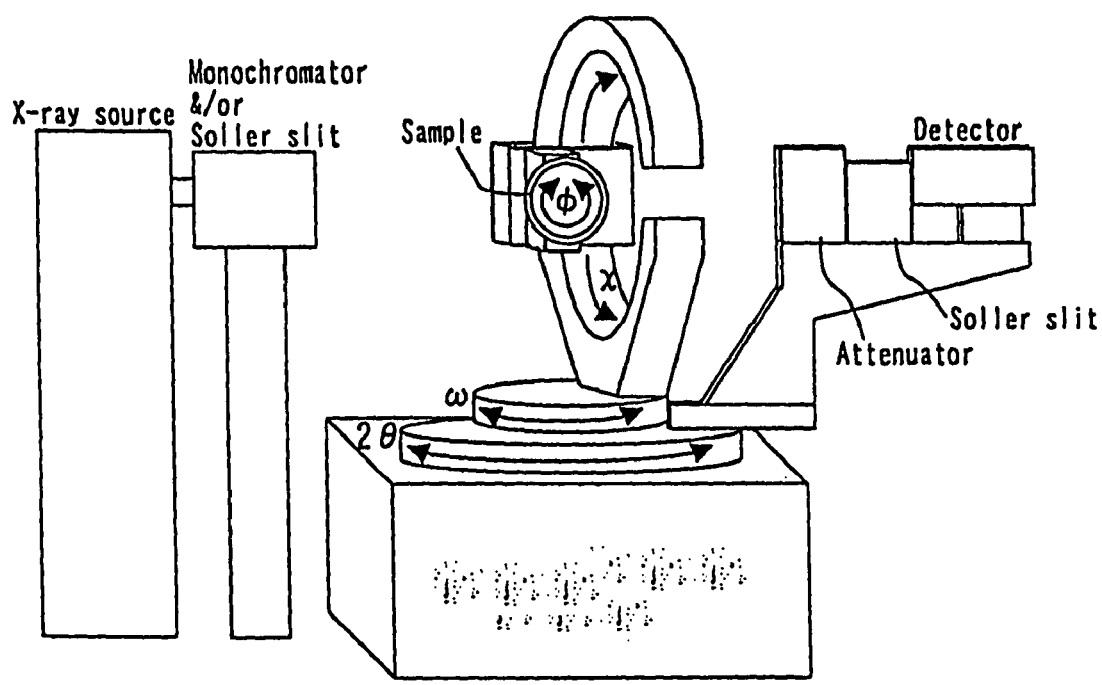
FIG. 15 schematically illustrates the ATX-E goniometer.

As shown in FIG. 15, the ATX-E goniometer has, as rotation axes, an $\Omega$ axis which is the vertical instrument axis, a X circle which lies in the vertical plane including the $\Omega$ axis and whose rotation axis passes through the instrument center, and a $\Phi$ axis which is permitted to be set at an angle $\chi$ along the X circle. The $\Phi$ shaft is supported from the X circle, and the crystal sample is attached to this $\Phi$ shaft so that it can be rotated around the $\Phi$ axis.

For this ATX-E goniometer, the UB matrix can be expressed as follows:

UB matrix=crystal orientation matrix U×crystal lattice matrix B where $$U = \begin{pmatrix} u_{xx} & u_{xy} & u_{xz} \\ u_{yx} & u_{yy} & u_{yz} \\ u_{zx} & u_{zy} & u_{zz} \end{pmatrix},$$

$$B = \begin{pmatrix} a^* & b^*\cos\gamma^* & c^*\cos\beta \\ 0 & b^*\sin\gamma^* & -c^*\sin\beta^*\cos\alpha \\ 0 & 0 & 1/c \end{pmatrix},$$

a,b,c,α,β,γ: lattice constants of the crystal,
a*,b*,c*,α*,β*,γ*: reciprocal lattice constants of the crystal,
a,b,c: vectors of the lattice constants,
a*,b*,c*: vectors of the reciprocal lattice constants, $$a = \begin{pmatrix} a_x \\ a_y \\ a_z \end{pmatrix}, b = \begin{pmatrix} b_x \\ b_y \\ b_z \end{pmatrix}, c = \begin{pmatrix} c_x \\ c_y \\ c_z \end{pmatrix},$$

$$a^* = \begin{pmatrix} a_x^* \\ a_y^* \\ a_z^* \end{pmatrix} = \frac{b \times c}{a \cdot (b \times c)}, b^* = \begin{pmatrix} b_x^* \\ b_y^* \\ b_z^* \end{pmatrix} = \frac{c \times a}{a \cdot (b \times c)},$$

$$\text{and } c^* = \begin{pmatrix} c_x^* \\ c_y^* \\ c_z^* \end{pmatrix} = \frac{a \times c}{a \cdot (b \times c)}.$$

And, the rotation matrix R can be expressed as follows:

$$R(\omega,\chi,\phi) + \Omega(\omega)X(\chi)\Phi(\phi)$$

where $$\Omega(\omega) = \begin{pmatrix} \cos\omega & \sin\omega & 0 \\ -\sin\omega & \cos\omega & 0 \\ 0 & 0 & 1 \end{pmatrix},$$

$$X(\chi) = \begin{pmatrix} \cos\chi & 0 & \sin\chi \\ 0 & 1 & 0 \\ -\sin\chi & 0 & \cos\chi \end{pmatrix},$$

$$\Phi(\phi) = \begin{pmatrix} 1 & 0 & 0 \\ 0 & \cos\phi & \sin\phi \\ 0 & -\sin\phi & \cos\phi \end{pmatrix},$$

ω: rotation angle of the crystal sample along Ω axis,
χ: rotation angle of the crystal sample along X axis, and
φ: rotation angle of the crystal sample along Φ axis.

With this rotation matrix R, when a value of the rotation angle ω is designated as one of the diffraction conditions of the designated Bragg reflection, values of the rotation angle χ and the rotation angle φ can be calculated by using the designated value of the rotation angle ω with the following equations:

$$\chi = \pm\cos^{-1}\left\{\frac{\cos\chi_0}{\cos(\omega-\omega_0)}\right\}$$

$$\phi = \phi_0 \pm \tan^{-1}\left\{\frac{\sin(\omega-\omega_0)}{\cos(\omega-\omega_0)\cdot\sin(\pm\chi)}\right\}$$

where
if χ≧0, then +,
and
if χ<0, then −.

Then, the rotation matrix R can be calculated by using the designated value of the rotation angle ω and the calculated values of the rotation angle χ and the rotation angle φ.

In another case, when a value of the rotation angle χ is designated as one of the diffraction conditions of the designated Bragg reflection, values of the rotation angle ω and the rotation angle φ can be calculated by using the designated value of the rotation angle χ with the following equations:

$$\omega = \omega_0 + \cos^{-1}\left\{\frac{\cos\chi_0}{\cos\chi}\right\}$$

$$\phi = \phi_0 \pm \tan^{-1}\left\{\frac{\sin(\omega-\omega_0)}{\cos(\omega-\omega_0)\cdot\sin(\pm\chi)}\right\}$$

where
if χ>0, then +,
and
if χ<0, then −.

Then, the rotation matrix R can be calculated using the designated value of the rotation angle χ and the calculated values of the rotation angle ω and the rotation angle φ.

In still another case, when a value of the rotation angle φ is designated as one of the diffraction conditions of the designated Bragg reflection, values of the rotation angle χ and the rotation angle ω can be calculated by using the designated value of the rotation angle φ with the following equations:

1) when $\chi = \pm 90°$, $$\omega = \omega_0 + \tan^{-1}\left(\frac{\sin(\phi_0-\phi)}{\pm\cos(\phi_0-\phi)}\right);$$

and 2) when $\chi \neq \pm 90°$, $$\chi = -\tan^{-1}\left\{\frac{\sin(-\chi_0)\cdot\cos(\phi_0-\phi)}{\cos(-\chi_0)}\right\}$$

$$\omega = \omega_0 + \tan^{-1}\left(\frac{\sin(-\chi_0)\cdot\sin(\phi_0-\phi)}{\frac{\cos(\chi_0)}{\cos(-\chi)}}\right).$$

Then, the rotation matrix R can be calculated by using the designated value of the rotation angle φ and the calculated values of the rotation angle χ and the rotation angle ω.

In the above equations, $\omega_0$, $\chi_0$ and $\phi_0$ can be obtained as follow:
if the coordinates of a reflection hkl of the crystal sample attached to the Φ shaft are indicated as $(x_0, y_0, z_0)$, then $$\omega_0 = \frac{2\theta_0}{2} = \text{Bragg angle};$$

1) when $\chi_0 < 0$, $$\begin{cases} \chi_0 = -\tan^{-1}\dfrac{\sqrt{y_0^2 + z_0^2}}{x_0} \\ \phi_0 = 180° - \tan^{-1}\dfrac{y_0}{z_0}, \text{ where if } y_0 = z_0 = 0 \text{ then } \phi_0 = 0°; \end{cases}$$

and 2) when $\chi_0 \geq 0$, $$\begin{cases} \chi_0 = \tan^{-1}\dfrac{\sqrt{y_0^2 + z_0^2}}{x_0} \\ \phi_0 = -\tan^{-1}\dfrac{y_0}{z_0}, \text{ where if } y_0 = z_0 = 0 \text{ then } \phi_0 = 0°. \end{cases}$$

Accordingly, the rotation matrix R can be obtained for the designated Bragg reflection as its Bragg reflection condition.

ATX-G Goniometer

Here, we explain about the UB matrix and the rotation matrix R for the ATX-G goniometer which is another diffractometer by this applicant.

Figure 16:
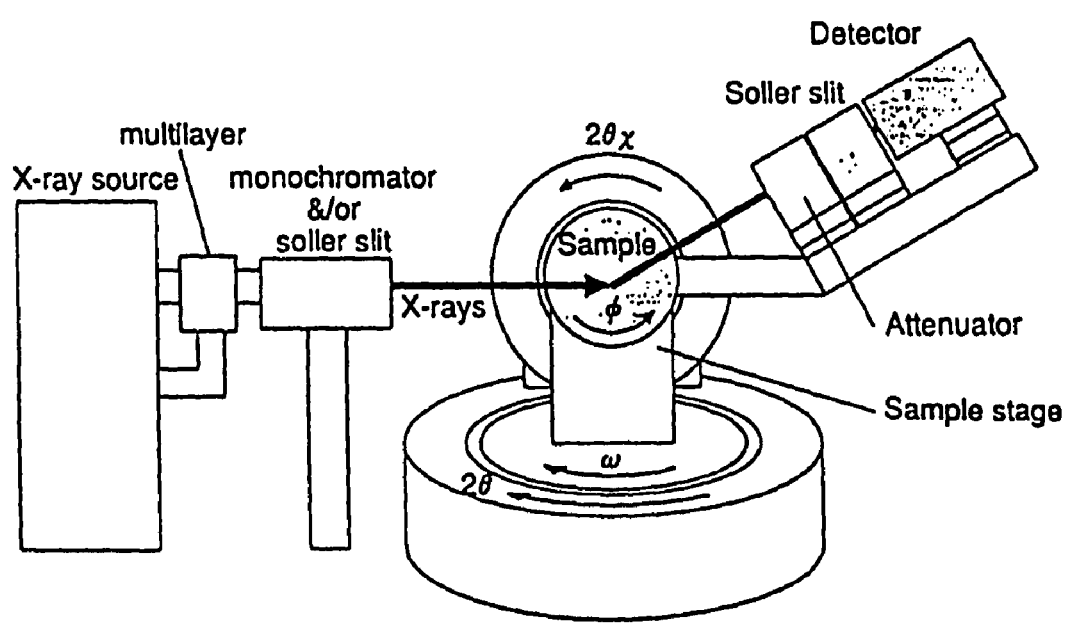
FIG. 16 schematically illustrates the ATX-G goniometer.

In the ATX-G of FIG. 16, the sample is rotated by an angle $\omega$ around an $\Omega$ axis which passes an origin of the sample surface. The detector is rotated by an angle $2\theta$ centering on the $\Omega$ axis along with the equatorial plane which intersects perpendicularly with the $\Omega$ axis and also rotated by and angle $2\theta \chi$ centering on the origin of the sample surface along with the plane on which the $\Omega$ axis lies and which intersects perpendicularly with the equatorial plane. And, the sample is also in-plane-rotated by an angle $\phi$ around a $\Phi$ axis which passes the origin of the sample surface and intersects perpendicularly with the sample surface.

For this ATX-G goniometer, the UB matrix can be expressed as same as that for ATX-E goniometer.

And, the rotation matrix R can be expressed as follows:

$$R = R_x(\delta_x)R_y(\delta_y)R_z(\delta_z)$$

where $$R_x(\delta_x) = \begin{pmatrix} 1 & 0 & 0 \\ 0 & \cos\delta_x & -\sin\delta_x \\ 0 & \sin\delta_x & \cos\delta_x \end{pmatrix},$$

$$R_y(\delta_y) = \begin{pmatrix} \cos\delta_y & 0 & \sin\delta_y \\ 0 & 1 & 0 \\ -\sin\delta_y & 0 & \cos\delta_y \end{pmatrix},$$

$$R_z(\delta_z) = \begin{pmatrix} \cos\delta_z & -\sin\delta_z & 0 \\ \sin\delta_z & \cos\delta_z & 0 \\ 0 & 0 & 1 \end{pmatrix},$$

$R_x$: rotation matrix along the coordinate axis x,
$R_y$: rotation matrix along the coordinate axis y, and
$R_z$: rotation matrix along the coordinate axis z.

With this rotation matrix R, when a value of the rotation angle $\omega$ is designated as one of the diffraction conditions of the designated Bragg reflection, values of the rotation angle $\phi$, the rotation angle $2\theta$ and the rotation angle $2\theta$ can be calculated by using the designated value of the rotation angle $\omega$ with the following equations:

$$\begin{cases} \phi = -\tan^{-1}\left\{ \dfrac{\dfrac{-2\sin^2\theta_0}{\lambda q_z\cos\omega} + \dfrac{q_x\sin\omega}{q_z\cos\omega} - \dfrac{q_y}{q_z}ans}{Ans} \right\} \text{ for } q_z > 0 \\ \phi = -\cos^{-1}q_x\sin\omega - \dfrac{2\sin^2\theta_0}{\lambda q_y\cos\omega} \text{ for } q_z \leq 0 \end{cases}$$

where $q_h(q_x,q_y,q_z)$: reciprocal lattice vectors of the designated diffraction plane h,
$\theta_0$: Bragg angle of the designated diffraction plane h,
Ans: answer below 1 among $ans_1$ and $ans_2$, $$ans_1 \text{ and } ans_2 \equiv x = \frac{-k_2 \pm \sqrt{k_2^2 - 4k_1k_3}}{2k_1},$$

$$k_1x^2 + k_2x + k_3 = 0, \text{ and}$$

$$\begin{cases} k_1 = \cos^2\omega(q_y^2 + q_z^2) \\ k_2 = -2q_y\cos\omega\left(\dfrac{-2\sin^2\theta_0}{\lambda} + q_x\sin\omega\right) \\ k_3 = \left(\dfrac{-2\sin^2\theta_0}{\lambda} + q_x\sin\omega\right)^2 - q_z^2\cos^2\omega. \end{cases}$$

$$2\theta\chi = 90° - \cos^{-1}\frac{s \cdot e_z}{|s|}$$

where $$q'_h = R_z(-\omega) \cdot R_x(\phi) \cdot q_h \equiv (q'_x, q'_y, q'_z), \text{ and}$$

$$\begin{cases} e_\omega = (0, 1/\lambda, 0) \\ e_x = (1, 0, 0), e_y = (0, 1, 0), e_z = (0, 0, 1) \\ s = q'_h + e_\omega \end{cases}.$$

$$2\theta = \cos^{-1}\left(\frac{2\theta_0}{2\theta\chi}\right)$$

where $\theta_0$: Bragg angle of the designated diffraction plane h.

Then, the rotation matrix R can be calculated by using the designated value of the rotation angle $\omega$ and the calculated values of the rotation angle $\phi$, the rotation angle $2\theta \chi$ and the rotation angle $2\theta$.

In another case, when a value of the rotation angle $2\theta$ is designated as one of the diffraction conditions of the designated Bragg reflection, values of the rotation angle $2\theta \chi$, the rotation angle $\phi$ and the rotation angle $\omega$ can be calculated by using the designated value of the rotation angle $2\theta$ with the following equations:

$$2\theta\chi = \cos^{-1}\left(\frac{2\theta_0}{2\theta}\right)$$

where
$\theta_0$: Bragg angle of the designated diffraction plane h.

$$\phi = \cos^{-1}(\text{Ans})$$

where
$q_h(q_x, q_y, q_z)$: reciprocal lattice vectors of the designated diffraction plane h,
$\theta_0$: Bragg angle of the designated diffraction plane h,
Ans: answer below 1 among $ans'_1$ and $ans'_2$, $$ans'_1 \text{ and } ans'_2 \equiv x = \frac{-k'_2 \pm \sqrt{k'^2_2 - 4k'_1 k'_3}}{2k'_1},$$

$k'_1 x^2 + k'_2 x + k'_3 = 0$, and $$\begin{cases} k'_1 = q_y^2 + q_z^2 \\ k'_2 = -\frac{2q_z \sin 2\theta_x}{\lambda} \\ k'_3 = \frac{\sin^2 2\theta_x}{\lambda^2} - q_y^2 \end{cases}.$$

$$\omega = \cos^{-1}(\text{Ans})$$

where
$q_h(q_x, q_y, q_z)$: reciprocal lattice vectors of the designated diffraction plane h,
$\theta_0$: Bragg angle of the designated diffraction plane h,
Ans: answer below 1 among $ans''_1$ and $ans''_2$.

$$ans''_1 \text{ and } ans''_2 \equiv x = \frac{-k''_2 \pm \sqrt{k''^2_2 - 4k''_1 k''_3}}{2k''_1},$$

$k''_1 x^2 + k''_2 x + k''_3 = 0$, and $$\begin{cases} k''_1 = (q_y \cos\phi + q_z \sin\phi)^2 + q_x^2 \\ k''_2 = \frac{4\sin^2 \theta_0 (q_y \cos\phi + q_z \sin\phi)}{\lambda} \\ k''_3 = \frac{2\sin^2 \theta_0}{\lambda^2} - q_x^2 \end{cases}.$$

Then, the rotation matrix R can be calculated by using the designated value of the rotation angle $2\theta$ and the calculated values of the rotation angle $2\theta \chi$, the rotation angle $\phi$ and the rotation angle $\omega$.

In still another case, when a value of the rotation angle $2\theta \chi$ is designated as one of the diffraction conditions of the designated Bragg reflection, values of the rotation angle $2\theta$, the rotation angle $\phi$ and the rotation angle $\omega$ can be calculated by using the designated value of the rotation angle $2\theta \chi$ with the following equations:

$$2\theta = \cos^{-1}\left(\frac{2\theta_0}{2\theta\chi}\right)$$

where
$\theta_0$: Bragg angle of the designated diffraction plane h.

$$\phi = \cos^{-1}(\text{Ans})$$

where
$q_h(q_x, q_y, q_z)$: reciprocal lattice vectors of the designated diffraction plane h,
$\theta_0$: Bragg angle of the designated diffraction plane h,
Ans: answer below 1 among $ans'''_1$ and $ans'''_2$, $$ans'''_1 \text{ and } ans'''_2 \equiv x = \frac{-k'''_2 \pm \sqrt{k'''^2_2 - 4k'''_1 k'''_3}}{2k'''_1},$$

$k'''_1 x^2 + k'''_2 x + k'''_3 = 0$, and $$\begin{cases} k'''_1 = q_y^2 + q_z^2 \\ k'''_2 = -\frac{2q_z \sin 2\theta_x}{\lambda} \\ k'''_3 = \frac{\sin^2 2\theta_x}{\lambda^2} - q_y^2 \end{cases}.$$

$$\omega = \cos^{-1}(\text{Ans})$$

where
$q_h(q_x, q_y, q_z)$: reciprocal lattice vectors of the designated diffraction plane h,
$\theta_0$: Bragg angle of the designated diffraction plane h,
Ans: answer below 1 among $ans''''_1$ and $ans''''_2$, $$ans''''_1 \text{ and } ans''''_2 \equiv x = \frac{-k''''_2 \pm \sqrt{k''''^2_2 - 4k''''_1 k''''_3}}{2k''''_1},$$

$k''''_1 x^2 + k''''_2 x + k''''_3 = 0$, and $$\begin{cases} k''''_1 = (q_y \cos\phi - q_z \sin\phi)^2 + q_x^2 \\ k''''_2 = \frac{4\sin^2 \theta_0 (q_y \cos\phi - q_z \sin\phi)}{\lambda} \\ k''''_3 = \frac{4\sin^2 \theta_0}{\lambda^2} - q_x^2 \end{cases}.$$

Then, the rotation matrix R can be calculated by using the designated value of the rotation angle $2\theta \chi$ and the calculated values of the rotation angle $2\theta$, the rotation angle $\phi$ and the rotation angle $\omega$.

In still another case, when a value of the rotation angle $\phi$ is designated as one of the diffraction conditions of the designated Bragg reflection, values of the rotation angle $\omega$, the rotation angle $2\theta\chi$ and the rotation angle $2\theta$ can be calculated by using the designated value of the rotation angle $\phi$ with the following equations:

$$\omega = \cos^{-1}(\text{Ans})$$

where
$q_h(q_x, q_y, q_z)$: reciprocal lattice vectors of the designated diffraction plane h,
$\theta_0$: Bragg angle of the designated diffraction plane h,
Ans: answer below 1 among $ans'''''_1$ and $ans'''''_2$, $$ans'''''_1 \text{ and } ans'''''_2 \equiv x = \frac{-k'''''_2 \pm \sqrt{k'''''^2_2 - 4k'''''_1 k'''''_3}}{2k'''''_1},$$

$k'''''_1 x^2 + k'''''_2 x + k'''''_3 = 0$, and

-continued $$\begin{cases} k_1'''' = (q_y \cos\phi + q_z \sin\phi)^2 + q_x^2 \\ k_2'''' = \dfrac{4\sin^2\theta_0(q_y\cos\phi + q_z\sin\phi)}{\lambda} \\ k_3'''' = \dfrac{4\sin^2\theta_0}{\lambda^2} - q_x^2 \end{cases}.$$

$$2\theta\chi = 90° - \cos^{-1} s \cdot \dfrac{e_z}{|s|}$$

where $q_h' = R_z(-\omega) \cdot R_x(\phi) \cdot q_h \equiv (q_x', q_y', q_z')$, and $$\begin{cases} e_\omega = \left(0, \dfrac{1}{\lambda}, 0\right) \\ e_x = (1,0,0), e_y = (0,1,0), e_z = (0,0,1) \\ s = q_h' + e_\omega \end{cases}$$

$$2\theta = \cos^{-1}\left(\dfrac{2\theta_0}{2\theta_\chi}\right)$$

where $\theta_0$: Bragg angle of the designated diffraction plane h.

Then, the rotation matrix R can be calculated by using the designated value of the rotation angle $\phi$ and the calculated values of the rotation angle $\omega$, the rotation angle $2\theta\chi$ and the rotation angle $2\theta$.

Accordingly, the rotation matrix R can be obtained for the designated Bragg reflection as its Bragg reflection condition.

Display of a Diffraction Plane

In addition, the present invention can display a diffraction plane on which the designated Bragg reflection locates and a reciprocal lattice point of the designated Bragg reflection on a display device by multiplying the above-calculated matrixes R, U and B and using its results.

More specifically, in order to perform such display, the following equation must be calculated:

$$\begin{pmatrix} x^* \\ y^* \\ z^* \end{pmatrix} = U'B \cdot \begin{pmatrix} h \\ k \\ l \end{pmatrix}$$

$$= RU \cdot B \cdot \begin{pmatrix} h \\ k \\ l \end{pmatrix}.$$

The multiplication of the matrix R to the matrix U of the UB matrix expresses rotation of the crystal in accordance with the rotation angles expressed in the matrix R. Thus, x*, y* and z* of this equation express a position in the reciprocal space of the crystal rotated in accordance with the rotation matrix R. In other words, x*, y* and z* express a position of the reciprocal lattice point to which the designated Bragg reflection occurs when the crystal is rotated in accordance with the rotation matrix R. Therefore, the diffraction plane on which x*, y* and z* locate is displayed on the display device, and the reciprocal lattice point is displayed at the position of x*, y* and z* within the diffraction plane on the display device.

As described above, any Bragg reflection conditions of any Bragg reflections for any crystal samples desired by an operator of the invention can be obtained and displayed according to the present invention.

Of course, the invention can measure a designated Bragg reflection by using the above-described device. For this measurement, the CPU drives the diffraction measurement device to rotate its rotation axes to have same rotation angles as the rotation matrix R calculated as above and then also drives the diffraction measurement device to measure the designated Bragg reflection.

In conclusion, the diffraction condition simulation device, the diffraction measurement system, and the crystal analysis system of this invention can have great effects on analysis of crystal structures and structure evaluation of single crystals including semiconductor thin films and the others.

This invention should not be limited only to the aforementioned embodiments, and it will be understood by those skilled in the art that other changes in form and details may be made therein without departing from the spirit and scope of the invention.

What is claimed is:

1. A diffraction condition simulation device for calculating a reciprocal lattice to a crystal sample and displaying, on a computer screen, Bragg reflection conditions of X rays or particle beams caused by the crystal sample, the diffraction condition simulation device comprising:

means for inputting and storing intrinsic crystal information;

means for inputting non-intrinsic sample information to determine an orientation of a simulated crystal sample;

means for calculating coordinates of all reciprocal lattice points within a limiting sphere of the simulated crystal sample using the intrinsic crystal information and the non-intrinsic sample information;

means for displaying, on the computer screen, a cross-section of the limiting sphere which intersects with a diffraction plane, and all reciprocal lattice points contained within the cross-section; and means for adjusting an orientation of the simulated crystal sample, wherein the displayed reciprocal lattice points rotate with a rotation of the simulated crystal sample such that previously calculated reciprocal lattice points are placed and displayed on the diffraction plane continuously during rotation.

2. A diffraction condition simulation device according to claim 1, wherein the means for displaying is operable to display all diffraction conditions which one of a plurality of Bragg reflections satisfies, on the computer screen, when a crystal of the simulated crystal sample is rotated along an axis connecting an origin of the reciprocal lattice to one of the reciprocal lattice points.

3. A diffraction condition simulation device according to claim 1, wherein the simulated crystal sample is rotated in correspondence to a moving direction of a pointer on the computer screen, and the reciprocal lattice in the limiting sphere is rotated with the rotation of the simulated crystal sample.

4. A diffraction condition simulation device according to claim 1, further comprising slide selecting means for selecting numerical values of an $\omega$ angle, a $\chi$ angle, and a $\phi$ angle of orientation of the simulated crystal sample displayed on the computer screen, the simulated crystal sample is rotated by sliding the slide selecting means, and the reciprocal lattice in the limiting sphere is rotated with the rotation of the orientation of the simulated crystal sample.

5. A diffraction condition simulation device according to claim 1, wherein each of the reciprocal lattice points in the cross-section of the limiting sphere is displayed together with its Miller indices on the computer screen.

6. A diffraction condition simulation device according to claim 1, wherein the means for calculating is further operable to calculate the structure factor of each of the reciprocal lattice points of the crystal sample within the limiting sphere.

7. A diffraction condition simulation device according to claim 6, wherein the means for calculating is operable to calculate the structure factor by calculating a crystal lattice matrix B of a UB matrix by using stored lattice constants of the simulated crystal sample, the crystal lattice matrix B representing a lattice of the simulated crystal sample and an initial orientation of the simulated crystal sample.

8. A diffraction simulation device according to claim 6, wherein the means for displaying is operable to display each of the reciprocal lattice points in the cross-section of the limiting sphere such that any differences in magnitude of the structure factors of the reciprocal lattice points are apparent from on the computer screen.

9. A diffraction condition simulation device according to claim 6, wherein the structure factor of a desired reciprocal lattice point among the reciprocal lattice points in the cross-section of the limiting sphere is displayed by specifying the desired reciprocal lattice point.

10. A diffraction condition simulation device according to claim 6, further comprising means for calculating an intensity at each reciprocal lattice point, using the structure factor associated with the respective reciprocal lattice point, and differentiating reciprocal lattice points having a general reflection from reciprocal lattice points having a forbidden reflection.

11. A diffraction condition simulation device according to claim 6, wherein Miller indices of each of the reciprocal lattice points is arranged in order of magnitude of the structure factor.

12. A diffraction condition simulation device according to claim 11, wherein the cross-section of the limiting sphere containing a desired reciprocal lattice point among the reciprocal lattice points is displayed by specifying the Miller indices of the desired reciprocal lattice point.

13. A diffraction condition simulation device according to claim 1, wherein Miller indices of each of the reciprocal lattice points is arranged in order of size of its Bragg angle.

14. A diffraction condition simulation device according to claim 1, wherein the means for displaying is operable to enlarge a peripheral region containing one or more of the reciprocal lattice points.

15. A diffraction condition simulation device according to claim 1, further comprising means for inverting directions of incident and outgoing reflection beams for X rays or particle beams.

16. A diffraction condition simulation device according to claim 1, wherein at least one of an incident angle of X rays to the simulated crystal sample, an outgoing angle from the simulated crystal sample, a $\chi$ angle of the simulated crystal sample, a $\phi$ angle of the simulated crystal sample, and an $\omega$ angle of the simulated crystal sample can be arbitrarily inputted.

17. A diffraction condition simulation device according to claim 16, wherein after one of a plurality of Bragg reflections is specified and at least one of the incident angle of the X rays to the simulated crystal sample, the outgoing angle from the simulated crystal sample, the $\omega$ angle of the simulated crystal sample, the $\phi$ angle of the simulated crystal sample, and the $\chi$ angle of the simulated crystal sample is input, all of the other angles are calculated for the specified Bragg reflection and displayed in the cross-section of the limiting sphere.

18. A diffraction condition simulation device according to claim 17, further comprising means for evaluating whether the $\omega$ angle, the $\phi$ angle, the $\chi$ angle, the incident angle and the outgoing angle exist in a blind region and newly calculating a symmetrical diffraction condition.

19. A diffraction measurement system comprising:
a diffraction condition simulation device for calculating a reciprocal lattice to a crystal sample and displaying, on a computer screen, Bragg reflection conditions of X rays or particle beams caused by the crystal sample, the diffraction condition simulation device comprising:
means for inputting and storing intrinsic crystal information;
means for inputting non-intrinsic sample information to determine an orientation of a simulated crystal sample;
means for calculating coordinates of all reciprocal lattice points within a limiting sphere of the simulated crystal sample using the intrinsic crystal information and the non-intrinsic sample information;
means for displaying, on the computer screen, a cross-section of the limiting sphere which intersects with a diffraction plane, and all reciprocal lattice points contained within the cross-section; and
means for adjusting an orientation of the simulated crystal sample,
wherein the displayed reciprocal lattice points rotate with a rotation of the simulated crystal sample such that previously calculated reciprocal lattice points are placed and displayed on the diffraction plane continuously during rotation; and
a device for measuring a Bragg reflection of X rays or particle beams by a crystal sample which satisfies a diffraction condition simulated by the diffraction condition simulation device.

20. A diffraction on measurement system according to claim 19, wherein a region in the vicinity of the Bragg reflection is measured in a mesh-like manner.

21. A crystal analysis system comprising:
a diffraction measurement system comprising:
a diffraction condition simulation device for calculating a reciprocal lattice to a crystal sample and displaying, on a computer screen, Bragg reflection conditions of X rays or particle beams caused by the crystal sample, the diffraction condition simulation device comprising:
means for inputting and storing intrinsic crystal information;
means for inputting non-intrinsic sample information to determine an orientation of a simulated crystal sample;
means for calculating coordinates of all reciprocal lattice points within a limiting sphere of the simulated crystal sample using the intrinsic crystal information and the non-intrinsic sample information;
means for displaying, on the computer screen, a cross-section of the limiting sphere which intersects with a diffraction plane, and all reciprocal lattice points contained within the cross-section; and means for adjusting an orientation of the simulated crystal sample, wherein the displayed reciprocal lattice points rotate with a rotation of the simulated crystal sample such that previously calculated reciprocal lattice points are placed and displayed on the diffraction plane continuously during rotation; and a device for measuring a Bragg reflection of X rays or particle beams by a crystal sample which satisfies a diffraction condition simulated by the diffraction condition simulation device; and analysis means for analyzing a crystal sample with the Bragg reflection measured by the diffraction measurement system.

* * * * *